US006951720B2

(12) United States Patent
Burgin, Jr. et al.

(10) Patent No.: US 6,951,720 B2
(45) Date of Patent: Oct. 4, 2005

(54) USE OF PHOSPHOROTHIOLATE POLYNUCLEOTIDES IN LIGATING NUCLEIC ACIDS

(75) Inventors: Alex B. Burgin, Jr., Bainbridge Island, WA (US); Lance J. Stewart, Bainbridge Island, WA (US)

(73) Assignees: San Diego State University Foundation, San Diego, CA (US); Emerald Biostructures, Incorporated, Bainbridge Island ( * ) Notice: Subject to any disclaimer, the term of this patent is extended or adjusted under 35 U.S.C. 154(b) by 313 days.

(21) Appl. No.: 09/882,274

(22) Filed: Jun. 15, 2001

(65) Prior Publication Data

US 2003/0165841 A1 Sep. 4, 2003

Related U.S. Application Data

(60) Provisional application No. 60/290,313, filed on May 10, 2001.

(51) Int. Cl.[7] ........................... C12Q 1/68; C12P 19/34; G01N 33/00; C07H 21/02; C07H 21/00
(52) U.S. Cl. ........................... 435/6; 435/91.1; 436/94; 536/23.1; 536/25.3
(58) Field of Search .......................... 435/6, 91.1, 183; 436/94; 536/23.1, 24.3, 24.33

(56) References Cited

U.S. PATENT DOCUMENTS

| | | | | |
|---|---|---|---|---|
| 5,256,568 A | * | 10/1993 | Panayotatos | 435/252.33 |
| 5,476,930 A | * | 12/1995 | Letsinger et al. | 536/25.3 |
| 5,766,891 A | | 6/1998 | Shuman | 435/91.41 |
| 5,843,648 A | * | 12/1998 | Robbins et al. | 435/6 |
| 6,013,445 A | * | 1/2000 | Albrecht et al. | 435/6 |

OTHER PUBLICATIONS

Burgin et al., "A novel suicide substrate for DNA topoisomerases and site–specific recombinases," *Nucleic Acids Res.* 23:2973–9 (1995).
Burgin and Nash, "Suicide substrates reveal properties of the homology–dependent steps during integrative recombination of bacteriophage λ," *Current Biol.* 5:1312–1321 (1995).
Cheng et al., "Conservation of structure and mechanism between Eukaryotic Topoisomerase I and site–specific Recombinases," *Cell* 92:841–50 (1998).
Christiansen et al., "The covalent eukaryotic topoisomerase I–DNA intermediate catalyzes pH–dependent hydrolysis and alcoholysis," *J Biol. Chem.* 269:11367–73 (1994).
"Directional TOPO Expression," *Expressions*, 7:2–3 (2000).
Genbank Accession No.: XM_018038.
Hamm and Piccirilli, "Synthesis and Characterization of Oligonucleotides Containing 2'–S,3'O–Cyclic Phosphorothiolate Termini," *J. Org. Chem.* 64:5700–5704 (1999).
Hwang et al., "DNA Contacts Stimulate Catalysis by a Poxvirus Topoisomerase," *J. Biol. Chem.* 274:9160–9168 (1999).

Krogh and Shuman, "DNA strand transfer catalyzed by vaccinia topoisomerase: peroxidolysis and hydroxylaminolysis of the covalent protein–DNA intermediate," *Biochemistry* 39:6422–32 (2000).
Mag et al., "Synthesis and selective cleavage of an oligodeoxynucleotide containing a bridged internucleotide 5'–phosphorothioate linkage," *Nucleic Acids Res.* 19:1437–41 (1991).
Pan et al., "Ligation of synthetic activated DNA substrates by site–specific recombinases and topoisomerase I," *J Biol. Chem.* 268:3683–9 (1993).
Petersen and Shuman, "DNA strand transfer reactions catalyzed by vaccinia topoisomerase: hyudrolysis and glycerololysis of the covalent protein—DNA intermediate," *Nucleic Acids Res.* 25:2091–97 (1997).
Redinbo et al., "Crystal structures of human topoisomerase I in covalent and noncovalent complexes with DNA," *Science* 279:1504–13 (1998).
Sekiguchi et al., "Kinetic Analysis of DNA and RNA Strand Transfer Reactions Catalyzed by Vaccinia Topoisomerase," *J. Biol. Chem.* 272:15721–728 (1997).
Sekiguchi and Shuman, "Site–specific ribonuclease activity of eukaryotic DNA topoisomerase I," *Mol. Cell* 1:89–97 (1997).
Shuman, Steward, "Novel Approach to Molecular Cloning and Polynucleotide Synthesis Using Vaccinia DNA Topoisomerase," *J. Biol. Chem.* 269:32678–84 (1994).
Shuman, Stewart, Polynucleotide Ligase Activity of Eukaryotic Topoisomerase I, *Mol. Cell* 1:741–748 (1998).
Woodfield et al., "Vaccinia topoisomerase and Cre recombinase catalyze direct ligation of activated DNA substrates containing a 3'–para–nitrophenyl phosphate ester," *Nucleic Acids Res.* 28:3323–31 (2000).

* cited by examiner

Primary Examiner—Kenneth R. Horlick
Assistant Examiner—Frank W Lu
(74) Attorney, Agent, or Firm—McDermott Will & Emery LLP

(57) ABSTRACT

The invention provides a method of nonenzymatic ligation of a nucleic acid. The method consists of contacting a polynucleotide-3' phosphorothiolate with an acceptor polynucleotide under conditions that allow formation of a phosphodiester bond between the polynucleotide-3' phosphorothiolate and the acceptor polynucleotide. The invention also provides methods of molecular cloning. In one embodiment, the method consists of contacting an insert comprising a polynucleotide-3' phosphorothiolate with an acceptor vector under conditions that allow formation of a phosphodiester bond between the insert and the acceptor vector to generate a vector comprising an insert polynucleotide. The invention further provides a compound consisting of a polynucleotide-3' phosphorothiolate and a kit containing a polynucleotide-3' phosphorothiolate. Also provided is a method of ligating a nucleic acid using a non-sequence specific topoisomerase.

16 Claims, 8 Drawing Sheets

OPS of TopoI cleavage site

TCRIBamS: 5' AATTCGCGGCCGCAAAAAGACTT-GATC 3'
TCRIBamAS: 3'         GCGCCGGCGTTTTTCTGAA-CTAG-DMT 5'

Figure 3A

OPS of TopoI cleavage site

TCRBstBS: 5' AATTCGCGGCCGCAAAAAGACTT-CG 3'
TCRBstBAS: 3'         GCGCCGGCGTTTTTCTGAA-GC-DMT 5'

Figure 3B

TCRIBamS: 5' AATTCGCGGCCGCAAAAAGACTTGATC 3'
TCRIBamAS: 3'         GCGCCGGCGTTTTTCTGAACTAG 5'

Figure 3C

GATC removed on topo cleavage to give BamHI compatible 5' overhang
5' AATTCGCGGCCGCAAAAAGACTTGATCAAGTCTTTTTGCGGCCGCG 5'
3'       GCGCCGGCGTTTTTCTGAACTAGTTCAGAAAAACGCCGGCGCTTAA 3'

Figure 3D

"↓" indicates site of topo cleavage
Oligo pair 4: TCR1BstBS + TCRABstBAS-DMT
Oligo pair 5: TCR1BstBS + TCRABstBAS
Oligo pair 6: TCR1BstBS + TCRABstBAS-P

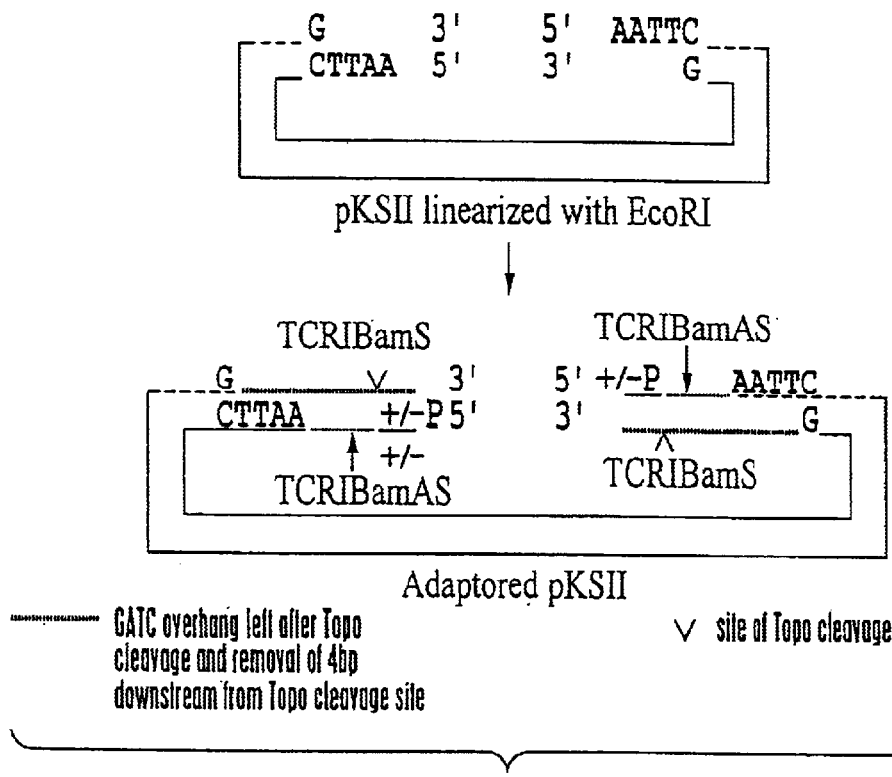
Figure 6A
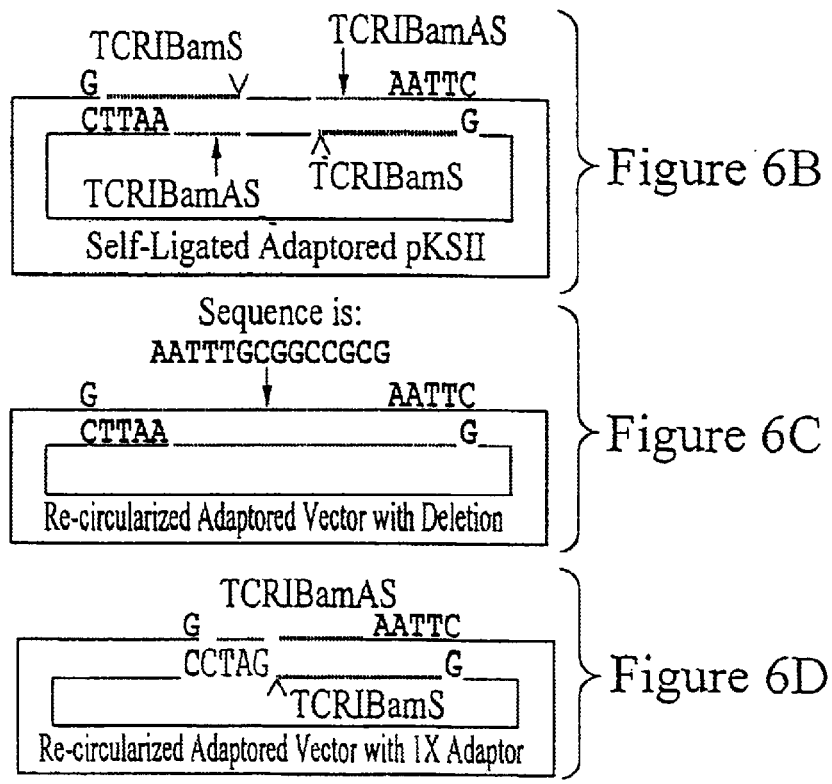
Figure 6B
Figure 6C
Figure 6D

USE OF PHOSPHOROTHIOLATE POLYNUCLEOTIDES IN LIGATING NUCLEIC ACIDS

This application claims the benefit of U.S. Provisional Application No. 60/290,313, filed May 10, 2001, and is incorporated herein by reference.

This invention was made with government support under grant number GM58596-02 awarded by the National Institutes of Health. The United States Government has certain rights in this invention.

BACKGROUND OF THE INVENTION

This invention relates generally to molecular cloning and, more specifically, to ligating polynucleotides.

The techniques of molecular cloning are used in virtually all realms of scientific research, from anthropology to forensic science to drug discovery. The role of molecular cloning in scientific research is expanding into new territory and increasing in importance, especially as techniques of molecular cloning are becoming easier to access and perform. The sequencing of the human genome is a prominent example of the contribution of molecular cloning to both basic science and medical research. The techniques of molecular cloning will also be central in the next phase of the human genome project, uncovering the functions of hundreds of newly identified human genes. This phase of the project will yield insights into the underlying causes of human disease, resulting in improved diagnostics and therapeutics. Increased efficiency in molecular cloning methods will accelerate progress in this, as well as many other areas of scientific endeavor.

Ligation of polynucleotides is a key step in the process of molecular cloning. Ligation is the joining of two nucleic acid molecules by the formation of a phosphodiester bond, which is the naturally occurring linkage between the nucleotides that make up a nucleic acid molecule. The ligation step in a molecular cloning procedure is typically performed using a ligase enzyme. This step is generally time-consuming because ligase enzymes can require incubation times of several hours to achieve optimal reaction efficiency. In recent years, a ligation method that works without a ligase enzyme has been developed and commercialized. The method employs a sequence specific viral topoisomerase enzyme. Although generally more time efficient, the "topo cloning" method is less flexible than standard cloning methods. For example, the method requires that a special sequence be incorporated into the DNA to be cloned. Further, "topo cloning" limits the user to a particular cloning site and therefore cannot be used for direct cloning of DNAs into user-selected restriction sites.

Thus, there exists a need for improved methods for ligating nucleic acids. The present invention satisfies this need and provides related advantages as well.

SUMMARY OF THE INVENTION

The invention provides a method of nonenzymatic ligation of a nucleic acid. The method consists of contacting a polynucleotide-3' phosphorothiolate with an acceptor polynucleotide under conditions that allow formation of a phosphodiester bond between the polynucleotide-3' phosphorothiolate and the acceptor polynucleotide.

The invention also provides methods of molecular cloning. In one embodiment, the method consists of contacting an insert comprising a polynucleotide-3' phosphorothiolate with an acceptor vector under conditions that allow formation of a phosphodiester bond between the insert and the acceptor vector to generate a vector comprising an insert polynucleotide. In another embodiment, the method of molecular cloning consists of contacting a vector comprising a polynucleotide-3' phosphorothiolate with an acceptor polynucleotide, under conditions that allow formation of a phosphodiester bond between the vector and the acceptor polynucleotide to generate a vector comprising the acceptor polynucleotide.

The invention further provides a compound consisting of a polynucleotide-3' phosphorothiolate and a kit containing a polynucleotide-3' phosphorothiolate. Such a kit can be used to ligate nucleic acids.

Also provided is a method of ligating a nucleic acid using a non-sequence specific topoisomerase. The method consists of contacting a polynucleotide-5' phosphorothiolate with a non-sequence specific topoisomerase, or a fragment or modification thereof, and an acceptor polynucleotide under conditions that allow formation of a phosphodiester bond between the polynucleotide-5' phosphorothiolate and the acceptor polynucleotide, with the proviso that the polynucleotide-5' phosphorothiolate does not contain the nucleotide sequence G(C/T)CCTT (SEQ ID NO:5).

The invention provides a composition containing a polynucleotide-5' phosphorothiolate and a non-sequence specific topoisomerase, and a kit containing a polynucleotide-5' phosphorothiolate and a non-sequence specific topoisomerase.

BRIEF DESCRIPTION OF THE DRAWINGS

FIG. 3A shows the nucleotide sequence of each strand of duplex substrate TCRIBamS/TCRIBamAS (SEQ ID NOS:8 and 9). FIG. 3B shows the nucleotide sequence of each strand of duplex substrate TCRIBstBS/TCRIBstBAS (SEQ ID NOS:10 and 11). FIG. 3C shows the duplex oligonucleotide product generated by Topo65 cleavage of a TCRIBamS/TCRIBamAS duplex substrate (SEQ ID NOS:14 and 15). FIG. 3D shows the nucleotide sequence of two cleaved TCRIBamS/TCRIBamAS oligonucleotide products ligated at a GATC overhang (SEQ ID NOS:16 and 17).

FIG. 6A is a schematic representation of a vector adapted with polynucleotide-5' phosphorothiolate oligonucleotides. FIGS. 6B, 6C and 6D show a schematic representation of plasmids generated by Topo65-mediated recircularization of adapted linear plasmid DNA.

DETAILED DESCRIPTION OF THE INVENTION

Figure 1:
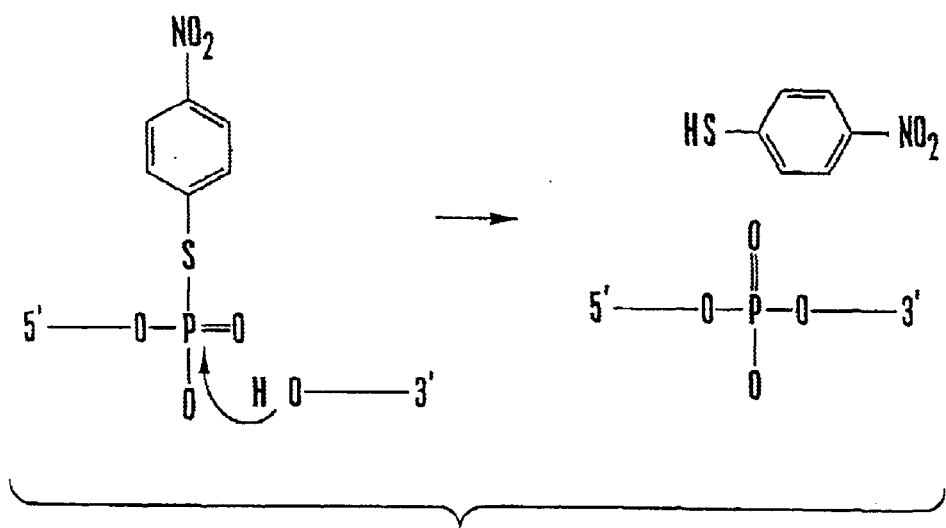
FIG. 1 is a schematic representation of the reaction mechanism of polynucleotide-3' phosphorothiolate ligation to an acceptor polynucleotide.

This invention is directed to methods of ligating a polynucleotide.

In one embodiment, the invention is directed to non-enzymatic ligation of polynucleotides. Non-enzymatic ligation of polynucleotides is achieved when a chemical reaction resulting in the formation of a phosphodiester bond occurs between a 3'-phosphorothiolate derivatized polynucleotide and an acceptor nucleic acid. In comparison with standard ligation methods that require an enzyme, non-enzymatic ligation provides the advantages of convenience, reduced cost and increased flexibility in designing reaction conditions. A polynucleotide-3' phosphorothiolate can be ligated to any complementary acceptor polynucleotide containing a 5'-OH group. Thus, a variety of polynucleotides can be ligated using the methods of the invention. For example, a polynucleotide-3' phosphorothiolate and acceptor polynucleotide can be RNA or DNA molecules, can be single or double stranded, can be linear, circular, or branched structures, and can contain a variety of functional domains, motifs, tags or moieties. The methods of the invention can be applied, for example, to generating RNA molecules, DNA molecules, RNA-DNA hybrids, vectors and inserts useful for molecular cloning, and complex polynucleotide structures.

In another embodiment, the invention is directed to topoisomerase-mediated ligation between a polynucleotide 5' phosphorothiolate and an acceptor nucleic acid. The method involves trapping a non-sequence specific topoisomerase on a polynucleotide by covalent binding of the enzyme to a 5'-phosphorothiolate moiety. A non-sequence specific topoisomerase bound to a polynucleotide 5' phosphorothiolate cleaves the polynucleotide strand at the 5'-phosphorothiolate site, generating a terminal end overhang. The topoisomerase can then ligate the bound polynucleotide to an acceptor polynucleotide having a complementary terminal end overhang.

Compared to a sequence specific topoisomerase which requires a defined recognition sequence to bind to and cleave a polynucleotide, a non-sequence specific topoisomerase has the advantage of allowing to user flexibility in the nucleic acid sequences present at the terminal ends of an insert polynucleotide. This flexibility allows the user to generate topoisomerase-bound polynucleotides having terminal end overhangs of their choice. Terminal end overhangs can be selected to accommodate any restriction endonuclease-generated terminal end overhang on an acceptor polynucleotide, allowing directional and non-direction ligation of an acceptor polynucleotide to a topoisomerase-bound polynucleotide.

As used herein, the term "ligation" is intended to mean the formation of a 5'-3' phosphodiester bond within a polynucleotide or between two or more polynucleotides. As used herein, the term "nonenzymatic ligation" is intended to mean ligation that occurs in the absence of an enzyme that catalyzes or facilitates the formation of a phosphodiester bond.

As used herein, the term "polynucleotide" is intended to mean a chain of two or more nucleotide 5'-monophosphate residues linked through one or more phosphodiester bonds. A nucleotide of a polynucleotide can contain a variety of glycose moieties, such as, for example, D-ribose and D-2-deoxyribose, as well as modified glycose moieties such as cytarabine. Therefore, a polynucleotide encompasses ribonucleic acid (RNA) or deoxyribonucleic acid (DNA), a hybrid of RNA and DNA, as well as RNA and DNA molecules containing nucleotides which have modified glycose moieties.

A nucleotide of a polynucleotide can contain any nucleic acid base, including both naturally occurring and modified bases. Examples of naturally occurring bases include guanine, adenine, thymine, cytosine and uridine. Examples of modified bases include 4-thio-uridine, pseudouridine, 2'-deoxy-uridine, 5-fluoro-uridine, 5-bromo-uridine, 5-iodo-uridine, 2'-amino-uridine, 2'-fluoro-uridine, 2'-fluoro-cytidine, 2'-amio-butyryl-pyrene-uridine, 5-fluoro-cytidine, ribo-thymidine, 5-methyl-cytidine, inosine, purine ribonucleoside, 2-aminopurine, 2,6-diaminopurine, $N^3$-methyl uridine and ribavirin. A variety of other structures can be incorporated into a synthetic base. For example, a base can contain 3' and 5' modifications such as 3'-puromycin, 3'-inverted deoxy thymidine, 3'-thioate linkage, 5'-fluorescein, 5'-biotin, 5'-Cy3, 5'-tetrachloro-fluorescein, and other moieties, with and without atomic spacers.

A polynucleotide can be naturally occurring or synthetically produced. For example, a polynucleotide can be isolated from an organism or synthesized using various methods, such as automated methods well known in the art. A naturally occurring polynucleotide can be, for example, an RNA such as an mRNA, a DNA such as a cDNA or genomic DNA, and can represent the sense strand, the anti-sense strand, or both.

A polynucleotide can be a single stranded, duplex or branched polynucleotide. As used herein, the term "duplex polynucleotide" is intended to mean a polynucleotide having two strands associated together by hydrogen bonding. A strand of a "duplex polynucleotide" can contain one or more mismatched, absent or additional nucleotides that do not associate with the cognate nucleotide in the partner strand, so long as the duplex remains associated under conditions that allow the formation of a phosphodiester bond between a polynucleotide-3' phosphorothiolate or a polynucleotide-5' phosphorothiolate and an acceptor polynucleotide. A duplex polynucleotide includes polynucleotides of both synthetic and natural origin. Thus, a duplex polynucleotide can be, for example, cDNA, genomic DNA, RNA, mRNA, synthetic DNA, including, for example, annealed complementary oligonucleotides or polynucleotides. A polynucleotide of natural origin can be derived from any eukaryotic, prokaryotic or viral source. Duplex DNA can have blunt ends, 3' terminal end overhangs and 5' terminal end overhangs. Duplex DNA can further contain a tag or moiety, such as a tag useful for detection or purification.

As used herein, the term "polynucleotide-3' phosphorothiolate" is intended to mean a polynucleotide that contains at least one 3'-phosphorothiolate moiety. As used herein, the term "3'-phosphorothiolate moiety" is intended to mean a nucleotide having at least one phosphate group linked by a phosphodiester bond at the 3' position of the sugar ring, the phosphate group having a phosphate oxygen substituted by sulfur. The sulfur can be bound to a chemical group, in particular a moiety results in the formation of a good leaving group.

A polynucleotide-3' phosphorothiolate is a compound having the following structure:

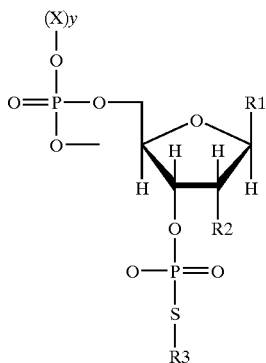

wherein,
X is a nucleotide;
Y is a positive integer;
R1 is a nucleotide base;
R2 is a hydrogen atom or hydroxyl; and
R3 is a halo, alkyl, substituted alkyl, sulfonate moiety, phenyl or substituted phenyl.

The term "alkyl" denotes such radicals as methyl, ethyl, n-propyl, isopropyl, n-butyl, sec-butyl, tert-butyl, amyl, tert-amyl, hexyl and the like. A preferred alkyl group is methyl.

The term substituted alkyl groups is intended to mean alkyl groups, such as C1 to C6 and C7 to C12 alkyl groups that are substituted by one or more halogen, hydroxy, protected hydroxy, oxo, protected oxo, cyclohexyl, naphthyl, amino, protected amino, (monosubstituted)amino, protected (monosubstituted)amino, (disubstituted)amino, guanidino, heterocyclic ring, substituted heterocyclic ring, imidazolyl, indolyl, pyrrolidinyl, $C_1$ to $C_7$ alkoxy, $C_1$ to $C_7$ acyl, $C_1$ to $C_7$ acyloxy, nitro, $C_1$ to $C_7$ alkyl ester, carboxy, protected carboxy, carbamoyl, carboxamide, protected carboxamide, N—($C_1$ to $C_6$ alkyl)carboxamide, protected N—($C_1$ to $C_6$ alkyl)carboxamide, N,N-di($C_1$ to $C_6$alkyl) carboxamide, cyano, methylsulfonylamino, thio, $C_1$ to $C_4$ alkylthio or $C_1$ to $C_4$ alkyl sulfonyl groups. The substituted alkyl groups may be substituted once or more with the same or with different substituents.

Examples of the above substituted alkyl groups include the chloromethyl, bromomethyl, iodomethyl, trifluoromethyl, 6-hydroxyhexyl, 2,4-dichloro(n-butyl), 2-aminopropyl, chloroethyl, bromoethyl, fluoroethyl, iodoethyl, chloropropyl, bromopropyl, fluoropropyl, iodopropyl and the like.

The term "substituted phenyl" specifies a phenyl group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl) carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl) amino or phenyl, substituted or unsubstituted, such that, for example, a biphenyl results.

Examples of the term "substituted phenyl" include a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(isopropyl)phenyl, 2, 3 or 4-ethylphenyl, 2, 3 or 4-(n-propyl) phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono-or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The terms "halo" and "halogen" refer to fluoro, chloro, bromo or iodo groups. An R3 group can contain one or more halogens, which are the same or different.

A sulfonate moiety can include, for example, a phenyl sulfonate, a substituted phenyl sulfonate, such as a halogen-substituted phenyl sulfonate, an alkyl sulfonate, such as methylsulfonate, and a substituted alkylsulfonate, such as trifluoromethylsulfonate. Sulfonate groups also include, for example, p-toluenesulfonates such as Tosyl, Brosyl, Mesyl, and Trifyl.

Therefore, a polynucleotide-3'phosphorothiolate of the invention can contain one of a variety of R3 groups which can function as a leaving group in a nonenzymatic ligation reaction. Exemplary R3 groups include the alkyl, substituted alkyl, phenyl, substituted phenyl, and alkyl, phenyl, substituted alkyl and substituted phenyl sulfonate groups shown below:

A trisubstituted alkyl, such as a halogen substituted alkyl, wherein R4 is any halogen or combination of halogen and hydrogen,

Trifluoromethyl.

A substituted phenyl, including a halogen-substitued phenyl, wherein R5 is any halogen, such as:

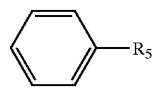

which can be, for example, fluorophenyl:

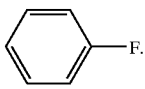

A trisubstituted phenyl, wherein R4 is any halogen or combination of halogen and hydrogen,

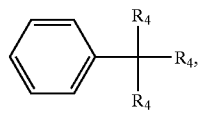

for example, trifluorophenyl,

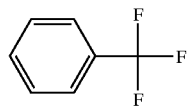

Other exemplary substituted phenyls include, for example:

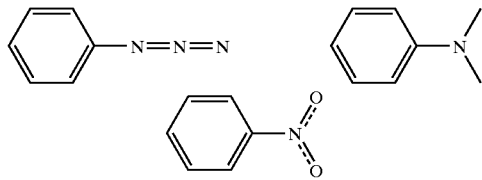

A trisubstituted alkylsulfonate, wherein R4 is any halogen or combination of halogen and hydrogen,

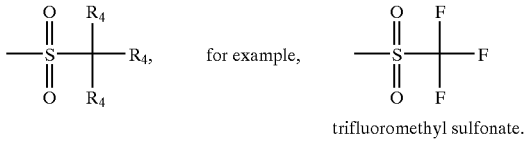

trifluoromethyl sulfonate.

A phenyl sulfonate, for example,

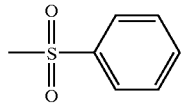

such as a substituted phenyl sulfonate, wherein R5 is a halogen, including, for example,

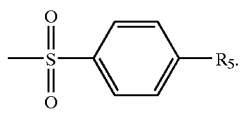

An exemplary substitued phenyl sulfonate is fluorophenyl sufonate:

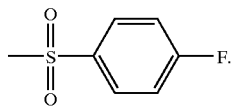

A polynucleotide-3' phosphorothiolate contains a phosphorothiolate moiety at the 3' carbon of the sugar ring of a nucleotide. The nucleotide is linked at its 5' carbon by a phosphodiester bond to another nucleotide, Xy. Since Y is a positive integer, the nucleotide X can be linked to any number of additional nucleotides. For example, a polynucleotide-3' phosphorothiolate can contain as few as two nucleotides, such as when y=1, to as many as thousands of nucleotides. The nucleotides can be naturally occurring, synthetic, modified, or a combination thereof.

As used herein the term "3'-SNP" is intended to mean a 3'-phosphorothiolate moiety in which the sulfur molecule is bound to a nitrophenyl, that is when R3=nitrophenyl.

As used herein the term "polynucleotide-3' phosphorothiolate precursor" is intended to mean a compound that undergoes a chemical reaction with an activator, as defined herein, to produce a polynucleotide-3' phosphorothiolate. A polynucleotide-3'phosphorothiolate precursor is a polynucleotide-3' phosphorothiolate in which the substituted sulfur molecule can undergo nucleophilic attack on an activator, displacing a molcule in the activator, and resulting in the formation of a distinct polynucleotide-3' phosphorothiolate. For example, polynucleotide-3' phosphorothiolate precursor can be a polynucleotide-3' phosphorothiolate wherein R3 is a hydrogen atom.

As used herein the term "activator" is intended to mean a compound or combination of compounds that undergoes a chemical reaction with a "polynucleotide-3' phosphorothiolate precursor" to produce a polynucleotide-3' phosphorothiolate. An activator contains a molecule that is displaced upon nucleophilic attack by a sulfur atom of a polynucleotide-3' phosphorothiolate precursor, resulting in the formation of a covalent bond between the activator and polynucleotide-3' phosphorothiolate precursor to produce a polynucleotide-3' phosphorothiolate. An activator therefore contains a molecule which can be displaced by a sulfur atom, such as, for example, iodine or bromine.

As used herein, the term "acceptor polynucleotide" is intended to mean a polynucleotide that contains a 5'-OH group that can form a phosphodiester bond with a nucleic acid. An acceptor polynucleotide can contain one or more 5'-OH groups that can form a phosphodiester bond with a nucleic acid. For example, an acceptor nucleic acid containing one 5'-OH group can ligate to one end of a nucleic acid, such as a 3'-phosphorothiolate polynucleotide or topoisomerase-bound 5'-phosphorothiolate polynucleotide. An acceptor nucleic acid containing a 5'-OH group at each terminal end can ligate to two ends of a nucleic acid, such as, for example, in cloning an insert into a circular nucleic acid such as a plasmid. A branched acceptor nucleic acid can contain one or more 5'-OH groups that can ligate to one or more nucleic acids to generate, for example, larger or more complexed branched nucleic acid species.

A acceptor polynucleotide can also comprise a polynucleotide 3'- or 5'-phosphorothiolate. For example, self-ligation can occur in a 3'- or 5'-polynucleotide phosphorothiolate containing an 5'-OH group that can form a phosphodiester bond.

As used herein, the term "non-sequence specific topoisomerase" refers to a class of enzymes, topoisomerase type I, found in both prokaryotes and eukaryotes which catalyze the interconversion of different topological isomers of DNA. An exemplary non-sequence specific topoisomerase is human topoisomerase I which has the amino acid sequence referenced as SEQ ID NO:2, encoded by the nucleotide sequence referenced as SEQ ID NO:1. These sequences are available in the Genbank database as accession number XM_018038. A non-sequence specific topoisomerase can cleave multiple different nucleic acid sequences and can be specifically targeted to a nucleic acid sequence of a polynucleotide 5'-phosphorothiolate. In contrast, a sequence specific topoisomerase cleaves primarily at a particular recognition sequence in a nucleic acid and does not substantially cleave non-recognition sequence containing nucleic acids.

Topoisomerases function in maintaining a specific DNA topology during nuclear processes such as transcription, replication, recombination, repair, chromatin assembly and chromosome segregation by cleaving and rejoining DNA strands. Topoisomerase I enzymes bind to and cleave only one of the two DNA strands, and ligate the strand to another DNA strand. Strand cleavage by type I topoisomerases occurs through transesterification of an active site tyrosine nucleophile to one strand of duplex DNA to generate a covalent DNA-(3'-phosphotyrosyl)-topoisomerase intermediate and a 5'-hydroxyl (5'-OH) DNA leaving group. Strand ligation by type I topoisomerases occurs through a second transesterification event in which a 5'-OH attacks the covalent DNA-(3'-phosphotyrosyl)-topoisomerase intermediate and displaces the topoisomerase. A "topoisomerase activity" therefore includes binding to a polynucleotide, polynucleotide strand cleavage and polynucleotide strand ligation.

The term topoisomerase encompasses native non-sequence specific topoisomerases from all species including non-sequence specific viral topoisomerases. The term "topoisomerase" also encompasses polypeptides containing minor modifications of a native topoisomerase sequence, and fragments of a full-length native topoisomerase, so long as the modified polypeptide or fragment retains one or more biological activities of a native topoisomerase, such as the abilities to bind to, cleave, and ligate DNA. A modification of a topoisomerase can include more additions, deletions, or substitutions of amino acids, so long as a biological activity of a native topoisomerase is retained. For example, a modification can serve to alter the stability or activity the polypeptide, or to facilitate its purification.

A modified topoisomerase can contain amino acid analogs, derivatives and mimetics. Such modifications and functional equivalents of amino acids are well known to those skilled in the art. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. For example, an organic structure which mimics arginine would have a positive charge moiety located in similar molecular space and having the same degree of mobility as the ε-amino group of the side chain of the naturally occurring amino acid. Those skilled in the art know or can determine what structures constitute functionally equivalent amino acid analogs and amino acid mimetics.

A "fragment" of a topoisomerase is intended to mean a portion of a topoisomerase that retains at least about the same activity as a native topoisomerase. A fragment of a topoisomerase can contain a modification. The Topo65 human topoisomerase I enzyme described herein is an exemplary fragment of a topoisomerase that contains a modification consisting of a polyhistidine tag.

The human topoisomerase I enzyme termed "Topo65" is encoded by the nucleic acid sequence referenced as SEQ ID NO:1. The Topo65 polypeptide contains amino acids 215 through 765 of human topoisomerase I, and is referenced as SEQ ID NO:2. Topo65 contains a series of six histidine residues incorporated at the amino terminus of the polypeptide, from amino acid residues 12 through 17.

The term "topoisomerase" includes recombinantly expressed topoisomerases expressed in cells or cell lysates, and includes chemically synthesized topoisomerases. A topoisomerase can contain an exogenous amino acid sequence, such as, for example, a tag that facilitates purification or identification. Exemplary tags include histidine tags, glutathione-S transferase tags, FLAG tags and myc tags. Other chemical tags such as biotin and fluorescent or radioactive tags can be present on a topoisomerase polypeptide or nucleic acid molecule.

The term "topoisomerase" excludes enzymes that are structurally distinct from a topoisomerase, but have enzymatic activities or reaction mechanisms similar to those of a topoisomerase. Therefore, the term "topoisomerase" specifically excludes enzymes such as integrases and recombinases, including for example, λ integrase, that cleave and ligate DNA but are structurally distinct from a topoisomerase of the invention.

The term "isolated", when used in reference to a topoisomerase of the invention is intended to mean a topoisomerase that is substantially removed or separated from components with which it is naturally associated.

The term "substantially the same amino acid sequence" when used in reference to a topoisomerase amino acid sequence is intended to mean an amino acid sequence having at least about 70% identity with respect to a reference amino acid sequence, and retaining comparable activity characteristic of the topoisomerase defined by the reference amino acid sequence. Polypeptides having "substantially the same amino acid sequence" will have at least about 80%, such as about 90% amino acid identity with respect to the reference amino acid sequence; including 95% and 98% amino acid identity with respect to the reference amino acid sequence. It is recognized, however, that polypeptides containing less than the described levels of sequence identity, arising as splice variants or that are modified by conservative amino acid substitutions are also encompassed within the scope of the present invention.

As used herein, the term "polynucleotide-5'phosphorothiolate" is intended to mean a compound having the following structure:

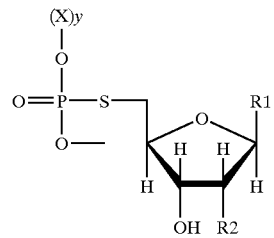

wherein,
X is a nucleotide;
Y is a positive integer;
R1 is a nucleotide base; and
R2 is a hydrogen atom or hydroxyl.

As shown, a polynucleotide-5' phosphorothiolate contains a phosphorothiolate moiety at the 5' carbon of the sugar ring of a nucleotide, forming a phosporothiolate linkage to a nucleotide, X. Since Y is a positive integer, a nucleotide can be linked to any number of additional nucleotides. For example, a polynucleotide-5' phosphorothiolate can contain as few as two nucleotides, such as when y=1, to as many as thousands of nucleotides. The nucleotides can be naturally occurring, synthetic, modified, or a combination thereof.

The term "polynucleotide-5' phosphorothiolate" specifically excludes polynucleotide molecules consisting of certain nucleotide sequences. In particular, the term "polynucleotide-5' phosphorothiolate" specifically excludes nucleic acid molecules containing the sequences G(C/T) CCTT (SEQ ID NO:5), AAA AAG ACT TAG AAA AAN NTT T, wherein N=5-bromo-deoxyuridine (SEQ ID NO:6), AAA AAG ACN NTG AAA AAN NNN T, wherein N=5-iodo-deoxyuridine (SEQ ID NO:7), AAA AAT NNN NCN AAG TCT TTN T, wherein N is 5-bromo-deoxyuridine (SEQ ID NO:12) and AAA AAT NNN NCA AAG TCT TTT T, wherein N is 5-iodo-deoxyuridine (SEQ ID NO:13).

As used herein, the term "vector" is intended to mean a DNA of any transmissible agent, such as a plasmid or virus, for example, into which a foreign DNA sequence can be spliced in order to introduce the foreign DNA into a host cell and promote its replication and transcription therein. A vector includes plasmid vectors, such as pBR322 and pUC vectors; bacteriophage vectors, such as λgt10 and λEMBL4; hybrid vectors, such as cosmids, phagemids, and phasmids; baculovirus and retroviral vectors; and vectors particularly useful for cloning large nucleic acid molecules, such as bacterial artificial chromosome vectors (BACs) and yeast artificial chromosome vectors (YACs). A vector can have a variety of features that render it useful for subcloning, sequencing, and expressing nucleic acids and polypeptides. For example, a vector can contain enhancer sequences, promotor sequences, transcription termination and RNA processing signals, an origin of replication, selectable marker genes and multiple cloning sites.

As used herein, the term "host cell" is intended to mean a cell that receives a polynucleotide. A host cell can be, for example, a bacterial, yeast, plant, insect, frog, fly, fish or mammalian cell that receives a polynucleotide. A variety of strains and types of host cells are included within the definition of "host cell." For example, a variety of strains of E. coli bacteria are routinely used for molecular cloning. Such strains include, for example, TOP10, BL21, NovaBlue and HB101.

As used herein, the term "terminal end overhang" is intended to mean one or more nucleotides of a single stranded portion of a duplex polynucleotide. A terminal end overhang can be present on a 3' or 5' end of a duplex polynucleotide.

The invention provides a method of ligating a nucleic acid. The method consists of contacting a polynucleotide-3' phosphorothiolate with an acceptor polynucleotide under conditions that allow formation of a phosphodiester bond between the polynucleotide-3' phosphorothiolate and the acceptor polynucleotide.

A polynucleotide 3-phosphorothiolate and acceptor polynucleotide are ligated together in the absence of any enzyme. Therefore, the methods of the invention involving ligating a polynucleotide 3-phosphorothiolate and an acceptor polynucleotide are also referred to as methods of non-enzymatic ligation.

A polynucleotide-3'phosphorothiolate, polynucleotide-5' phosphorothiolate, and acceptor polynucleotide can have a variety of physical and functional attributes, allowing the generation of diverse ligation products. As such, the methods of ligating a nucleic acid can be used to construct polynucleotides for a variety of applications, from basic molecular cloning to building specialized polynucleotide molecules or complexes of polynucleotide molecules. For example, a polynucleotide-3'phosphorothiolate, polynucleotide-5' phosphorothiolate and acceptor polynucleotide can be single or double stranded, branched, circular or linear polynucleotides. Accordingly, the methods of the invention can be used to ligate polynucleotide-3'phosphorothiolates or polynucleotide-5' phosphorothiolates and acceptor polynucleotides to produce, for example, synthetic RNAs and DNAs, RNA-DNA hybrids, nucleic acids having particular structures, including highly branched structures.

The methods of the invention for ligating a nucleic acid can be advantageously applied to molecular cloning. Either or both cloning vector and insert can contain a 3'phosphorothiolate moiety that enables non-enzymatic ligation with an acceptor polynucleotide. Single inserts, as well as multiple inserts, can be cloned into a vector. Thus, the molecular cloning methods of the invention can be used for routine cloning tasks as well as more complex cloning projects, such as, for example, gene synthesis.

A polynucleotide-3' phosphorothiolate mediates non-enzymatic ligation of a nucleic acid because the sulfur-phosphorus bond is labile, and is subject to attack by a 5'-OH group of an acceptor polynucleotide. A chemical group bound to the sulfur molecule such as, for example, an alkyl or phenyl halide, when bound to sulfur will form a good leaving group, such that the sulfur atom will be displaced, allowing the formation of a phosphodiester bond upon nucleophilic attack by a 5'-OH of an acceptor polynucleotide. As described herein, this mechanism of action was identified through detailed study of the mechanism of topoisomerase cleavage and ligation of nucleic acid suicide substrates.

A polynucleotide-3' phosphorothiolate to be ligated using the methods of the invention for non-enzymatic ligation can have a variety of chemical, structural and functional properties. Likewise a polynucleotide-5' phosphorothiolate can have a variety of chemical, structural and functional properties. For example, a polynucleotide-3' phosphorothiolate or polynucleotide-5' phosphorothiolate can be a DNA or RNA molecule, or hybrid of DNA and RNA, and can include modified glycose moieties, modified nucleic acid bases, and tags such as detection and purification tags. A hybrid of DNA can be, for example, a DNA strand bound to a complementary RNA strand, or a single polynucleotide strand containing both ribonucleic acids and deoxyribonucleic acids.

It can be desirable to prepare a hybrid polynucleotide containing DNA and 2'-O-methyl RNA, for example, to obtain enhanced nuclease resistance and increased binding affinity. Modified glycose moieties and nucleic acid bases can be incorporated into a polynucleotide-3' phosphorothiolate, for example, to facilitate detection or to alter the affinity of interaction with another molecule. Incorporating modified bases such as deoxyinosine and uridine into a DNA molecule can, for example, make duplexes with oligonucleotides more stable and can facilitate the preparation of degeneracy in primer sequences. In addition RNA polynucleotides, such as oligonucleotides, made with modified bases can have higher affinities for DNA without the inherent nuclease sensitivity and instability of RNA. The uses of modified nucleic acid bases are well known in the art.

Thus, methods of incorporating such modifications into a polynucleotide are known and there are many commercial sources for obtaining polynucleotides containing modified bases.

Tags and moieties, such as those useful for detection and purification of a polynucleotide, include, for example, a radiolabel, a fluorochrome, a ferromagnetic substance, a luminescent tag, molecular beacon, or a detectable binding agent such as biotin. Fluorescent tags such as fluorescein dyes, rhodamine dyes, BODIPY, and Cy3 or 5 dyes can be useful, for example, in antisence applications for tracking the intracellular location of a ligated product polynucleotide, in situ hybridization, PCR product detection and a variety of DNA fragment analysis protocols well known in the art. A tag such as biotin is useful for facilitating capture of a molecule using a streptavidin-coated medium, for example. Other tags, such as a primary amine, can be incorporated into a polynucleotide to make it receptive to incorporation with another tag or label. The use of a radioactive tag is described herein, in Example III.

A polynucleotide-3' phosphorothiolate can contain one or more incorporated 3'phosphorothiolate moieties. For example, a 3' phosphorothiolate moiety can be incorporated at a single 3' end of a single or double stranded polynucleotide, such as when it is desired to generate a linear polynucleotide ligation product, or at two 3' ends of a double stranded polynucleotide, such as when it is desired to generate a circularized ligation product, or when a plurality of polynucleotides are being ligated together to generate a linear or circular ligation product. A 3' phosphorothiolate moiety can also be incorporated into more than one 3' end of a branched polynucleotide, such as when it is desired to generate longer or more complex polynucleotide branches or extensions. Likewise, a polynucleotide-5' phosphorothiolate can contain one or more incorporated 5'phosphorothiolate moieties which can be incorporated into single stranded, double stranded and branched polynucleotides.

A polynucleotide-3' phosphorothiolate can be prepared, for example, by incorporating one or more 3'-phosphorothiolate moieties into a polynucleotide during synthesis of the polynucleotide, by ligating a polynucleotide-3' phosphorothiolate onto a particular polynucleotide, and by using one or more oligonucleotide polynucleotide-3' phosphorothiolates as PCR primers for amplifying a desired polynucleotide. When using one polynucleotide-3' phosphorothiolate primer, a second primer can contain a different moiety or tag, if desired. For example, a desired nucleic acid sequence can be amplified using one polynucleotide-3' phosphorothiolate primer and one polynucleotide-5' phosphorothiolate primer. A polynucleotide-5' phosphorothiolate can be prepared in the same manner by incorporating one or more 5'-phosphorothiolate moieties during synthesis or post-synthetically.

A polynucleotide-3' phosphorothiolate can also be generated from a polynucleotide-3' phosphorothiolate precursor by reacting the precursor with an activator. A polynucleotide-3' phosphorothiolate precursor contains a sulfur atom in a phosphorothiolate moiety capable of nucleophilic attack of a bond in an activator molecule to produce a polynucleotide-3' phosphorothiolate containing a substituted sulfur atom which acts as a good leaving group in the methods of the invention for non-enzymatic ligation of nucleic acids. For example, the sulfur atom of a polynucleotide-3' phosphorothiolate wherein R3 is a hydrogen atom, can displace an iodine atom from 4-iodo-nitrobenzene to produce a polynucleotide-3' phosphorothiolate wherein R3 is nitrophenyl (see Example VII). Therefore, an activator can be a compound having an atom which can be displaced by a sulfur atom bonded to an oxygen atom within a polynucleotide 3' phosphorothiolate, such as a compound having a halo which can be displace by nucleophilic attack. The selection of an activator will determine the R3 group bound to the polynucleotide 3'-phosphorothiolate sulfur. Therefore, an activator can be selected to generate a polynucleotide 3'-phosphorothiolate which contains a good leaving group. As described and depicted herein, R3 groups such as alkyl halides, phenyl halides, alkyl sulfonates and phenyl sulfonates can be good leaving groups for incorporation into a polynucleotide-3' phosphorothiolate. Activators which, upon reaction with a polynucleotide-3' phosphorothiolate precursor, produce polynucleotide-3' phosphorothiolates containing such R3 groups are well known to those skilled in the art. Such activators include, for example, iodo-nitrobenzene, iodo-trifluorobenzene and iodo-, bromo- or other derivatives of R3 moieties described herein.

It can be desirable to generate a polynucleotide-3' phosphorothiolate from a precursor, for example, when a precursor has greater stability, is more conveniently stored or packaged, or is produced at lower cost than a polynucleotide-3' phosphorothiolate. A polynucleotide-3' phosphorothiolate precursor can be used to generate a polynucleotide-3' phosphorothiolate prior to addition to an acceptor nucleic acid or in the presence of an acceptor nucleic acid, if desired. Any of the ligation methods of the invention that employ a polynucleotide-3' phosphorothiolate described herein can be performed with a polynucleotide-3' phosphorothiolate generated by reaction of a polynucleotide-3' phosphorothiolate precursor and an activator.

Conditions sufficient to react a polynucleotide-3' phosphorothiolate precursor and an activator will vary depending on the particular precursor and activator used. Those skilled in the art will understand how to select useful precursors and activators and will know, or can determine, how to obtain a particular precursor or activator. Conditions sufficient to react an exemplary polynucleotide-3' phosphosphorothiolate precursor, a polynucleotide-3' phosphorothioate, and an exemplary activator, 4-iodo-nitrophenyl, are described herein in Example VII.

A variety of analytical methods and functional assays well known in the art can be employed to determine if a particular synthesis method, including generation of a polynucleotide-3' phosphorothiolate by reaction with an activator, is useful for generating a desired polynucleotide-3' phosphorothiolate or polynucleotide-5' phosphorothiolate. For example, a synthetic product an be analyzed using standard methods such as NMR, mass spectroscopy and HPLC using appropriate standards, or assayed for ligation activity using various, such as those described herein.

Ligation of a polynucleotide-3' or 5' phosphorothiolate produces a product polynucleotide which does not contain a phosphorothiolate sulfur atom. Therefore, a ligated product can be conveniently separated from unligated phosphorothiolate sulfur-containing polynucleotide by a variety of separation methods, if desired. For example, sufur-containing polynucleotides can be removed from non-sulfur containing polynucleotides by absorption onto a chromatographic medium that binds sulfur. Exemplary sulfur-binding molecules which can be incorporated into separation media include heavy metals, such as mercury. Alternatively, various separation methods well known in the art, including methods based on isolating a polynucleotide containing a purification tag, can be emloyed when it is desired to separate ligated from non-ligated polynucleotides.

Non-enzymatic ligation occurs when an acceptor polynucleotide 5'-OH displaces the sulphur contained in the modified phosphodiester linkage of a polynucleotide-3' phosphorothiolate. Therefore, an acceptor polynucleotide contains at least one 5'-OH group. In addition to this characteristic, an acceptor polynucleotide to be ligated using the methods of ligating polynucleotides of the invention also can have a variety of chemical, structural functional properties. As described in reference to a polynucleotide-3' phosphorothiolate, an acceptor polynucleotide can be single stranded, duplex, or branched DNA, RNA or hybrid molecule, can contain a variety of modified glycose and nucleotide bases, and can contain additional useful tags or moieties.

An acceptor polynucleotide having one or more 5'-OH groups can be prepared using a variety of methods well known in the art. For example, methods such as cleavage of an acceptor polynucleotide with a restriction endonuclease and dephosphorylation using phosphatases such as bovine alkaline phosphatase and calf intestinal alkaline phosphatase can be used to generate a 5'-OH containing acceptor polynucleotide. A 5'-OH containing acceptor polynucleotide can also be synthesized using automated methods well known in the art. For example, a standard nucleic acid synthesis method typically involves protecting the 5'-OH group of a nucleic acid with a dimethoxytrityl (DMT) group. Deprotection of the synthesized polynucleotide results in the generation of a 5'-OH group. For example, a DMT group can be removed from a polynucleotide by detritylation with a dichloroacetic acid/trichloroacetic acid to generate a 5'-OH group. Preparation of polynucleotides containing a 5'-OH group is routine to those of skill in the art. Analytical methods well known in the art and functional assays, such as those described herein, can be used to determine if a polynucleotide contains a 5'-OH group.

The methods of the invention for ligating nucleic acids are performed by contacting a polynucleotide-3' phosphorothiolate with an acceptor polynucleotide. A polynucleotide-3' phosphorothiolate and acceptor polynucleotide can have similar or different chemical, structural and functional properties. For example, a polynucleotide-3' phosphorothiolate and acceptor polynucleotide can both be RNAs, DNAs, or hybrids, or can each have different chemical properties. Both a polynucleotide-3' phosphorothiolate and acceptor polynucleotide can be single stranded, double stranded or branched polynucleotides, or alternatively, can each have different structural properties. A polynucleotide-3' phosphorothiolate and acceptor polynucleotide can have similar or different functional properties. For example, both can be vectors or inserts, each having the same or different constituent functional features, such as promoters, enhancers, genes, and the like, or each can have different functional properties. Similarly, a polynucleotide-5' phosphorothiolate and acceptor nucleic acid can have similar or different chemical, structural and functional activities.

A duplex acceptor polynucleic can undergo non-enzymatic ligation so long as it is sufficiently complementary to base pair with a polynucleotide-3' phosphorothiolate or polynucleotide-5' phosphorothiolate. For example, polynucleotides having blunt ends, or complementary terminal end overhangs can undergo non-enzymatic ligation.

It can be advantageous to have complete complementarity between the terminal end overhangs of a polynucleotide-3' phosphorothiolate or polynucleotide-5' phosphorothiolate and an acceptor polynucleotide such that ligation occurs substantially between specific nucleic acids to allow predictable ligation products. However, having missing, extra or mismatched bases present in one terminal end overhang, does not preclude the generation of a replicatable plasmid in a host cell. For example, an acceptor polynucleotide that is ligated to a polynucleotide-3' phosphorothiolate to form a plasmid can be ligated to an insert only on the two 5' ends, only on the two 3' ends or on one 5' and one 3' end of the insert, transformation into a host cell can produce an intact vector due to repair of the plasmid within the host cell. Therefore, transformation of a ligated polynucleotide product into a host cell is useful for generating a polynucleotide product. Transformation of ligated polynucleotides into a host cell can optionally be used in any of the methods of the invention for ligating nucleic acids.

A variety of conditions are suitable for ligating a nucleic acid using the methods of the invention involving non-enzymatic ligation and topoisomerase-mediated ligation. Such conditions can include time of reaction, temperature of reaction, components in a reaction mixture and the particular concentration of each component in a reaction mixture. Non-enzymatic and topoisomerase-mediated ligation can occur over a range of reaction times, from several seconds, to several minutes, to several hours. The length of time required to generate ligated products will be influenced by the temperature and reaction mixture components. For example, the generation of ligated products will occur in a shorter time period when performed at a warm temperature, such as 37° C., compared to a cool temperature, such as 16° C. Times of incubation can therefore be about less that one hour, such as about one minute, about two to ten minutes, about 30 minutes to one hour, or more than one hour, including several hours, such as overnight. A non-enzymatic and topoisomerase-mediated ligation can occur over a range of temperatures. For example, using non-enzymatic ligation, ligated products can be produced at temperatures of between −20 to −5° C., −4 to 3° C., 4 to 15° C., 16 to 25° C., 26 to 36° C., 37 to 42° C., 42 to 50° C., 51 to 60° C., 60 to 75° C. and 76 to 100° C. For topoisomerase-mediated ligation, ligated products can be produced at temperatures of between 4 to 16° C., 16 to 25° C., 26 to 36° C., 37 to 42° C. and 42 to 50° C.

The methods of the invention for ligating polynucleotides can be performed in the presence of various chemical components. Exemplary chemical components include, for example, buffers such as Tris-HCL, Tris-acetate, potassium-acetate, magnesium acetate, Bis Tris propane-HCl, and potassium phosphate, salts such as NaCl, KCl, and MgCl2, proteins such as bovine serum albumin and IgG, detergents such as Triton X-100, CHAPS and SDS, metal chelators such as EDTA and EGTA, condensing reagents such as hexamminecobalt chloride, crowding reagents such as polyethylene glycol, oxidizing or reducing agents such as dithiothrietol and β-mercaptoethanol, non-reactive nucleic acids molecules such as tRNA, and other chemical components such as glycerol. One skilled in the art can readily determine a condition for that allows formation of a phosphodiester bond between a polynucleotide-3' phosphorothiolate or a polynucleotide-5' phosphorothiolate and an acceptor polynucleotide by performing the ligation reaction under a variety of time, temperature, and buffer composition conditions followed by detection of a ligated product. A ligation product can be detected by a variety of methods well known in the art, such as the SDS-PAGE methods described herein.

The invention provides a method of molecular cloning. The method consists of contacting an insert comprising a polynucleotide-3' phosphorothiolate with an acceptor vector under conditions that allow formation of a phosphodiester bond between the insert and the acceptor vector to generate a vector comprising an insert polynucleotide.

A polynucleotide-3' phosphorothiolate, such as an insert comprising a polynucleotide-3' phosphorothiolate can have various chemical, structural and functional properties, as described above. An insert can be of any size with respect to a recipient vector. For example, an insert can be a polynucleotide-3' phosphorothiolate having a few, tens, or hundreds of nucleic acids.

An insert comprising a polynucleotide-3' phosphorothiolate to be ligated to an acceptor polynucleotide can be blunt-ended or have terminal end overhangs complementary to a recipient vector. Selection of inserts and vectors having compatible or complementary terminal end overhangs is routine in the art, and is described, for example in and Russell, *Molecular Cloning: A Laboratory Manual*, Cold Spring Harbor Laboratory Press, Cold Spring Harbor, N.Y. (2001), which is incorporated herein by reference. In addition, it is well known in the art that ligation between certain non-complementary terminal ends can occur within a host cell. For example, a host such as *E. coli* can repair nicks in circular plasmids, fill in missing bases, and can remove an extra bases, such as those of a terminal end overhang, in vivo to produce a repaired, replicatable plasmid. Accordingly, transformation of a vector containing a partially ligated insert, such as an insert ligated only at 3' ends of the insert or vector, can result in in vivo repair and generation of a replicatable vector in a host cell.

An insert comprising a polynucleotide-3' phosphorothiolate can be prepared using a variety of methods, as described in relation to a polynucleotide-3' phosphorothiolate. For example, a polynucleotide-3' phosphorothiolate, such as an insert comprising a polynucleotide-3' phosphorothiolate, can be prepared by synthesing a polynucleotide portion using standard polynucleotide synthesis methods, and then chemically modifying the polynucleotide to incorporate a 3'-phosphorothiolate moiety. Alternatively, a 3'-phosphorothiolate moiety can be introduced into an insert by ligation, or an insert can be prepared by PCR using an oligonucleotide pair in which at least one oligonucleotide contains a 3'-phosphorothiolate moiety. A double-stranded insert comprising a polynucleotide-3' phosphorothiolate can be made by annealing a complementary polynucleotide strand that can optionally contain a 3'-phosphorothiolate moiety. Such methods can similarly be employed to prepare a polynucleotide-5'phosphorothiolate insert.

A duplex insert can be generated by annealing two complementary synthetic polynucleotides, one or both of which can be a polynucleotide-3' phosphorothiolate. Methods for annealing nucleic acids are well known in the art and an exemplary condition for annealing two oligonucleotides is described herein.

As described above in reference to a polynucleotide-3' phosphorothiolate, an insert polynucleotide-3' phosphorothiolate can likewise contain one or more 3' phosphorothiolate moieties. An acceptor vector to be ligated to an insert polynucleotide-3' phosphorothiolate also can also have chemical, structural and functional properties as described above for an acceptor polynucleotide. An acceptor vector, for example, can contain one or more 5-OH groups. A vector having one 5'-OH can be ligated to an insert to generate a linear vector comprising the insert. For duplex circular vector, such as a plasmid vector, it is advantageous to have a 5'-OH at each terminal end of the vector to generate an intact plasmid in a host cell, as described above. Ligation of the 3' ends of an acceptor vector can be obtained, for example, by incorporation of 3'-phosphorothiolate moieties at one or more 3' ends. Ligation can thereby occur between 5'-OH ends of the 3'-phosphorothiolate insert and the 3' ends of the vector. Such inserts and vectors containing both 5'-OH groups and 3'-phosphorothiolate moieties are designed to prevent or minimize self-ligation reactions, for example, by making 3' and 5' ends non-complementary.

The invention also provides a method of molecular cloning in which a vector contains a polynucleotide-3' phosphorothiolate. The method consists of contacting a vector containing a polynucleotide-3' phosphorothiolate with an acceptor polynucleotide, under conditions that allow formation of a phosphodiester bond between the vector and the acceptor polynucleotide to generate a vector containing the acceptor polynucleotide.

As described herein, in reference to a polynucleotide-3' phosphorothiolate, a vector containing a polynucleotide-3' phosphorothiolate can have one or more 3'-phosphorothiolate moieties incorporated at one or more 3'- or 5'-ends. Therefore, one or more phosphodiester bonds can be formed between a vector and an insert. For a plasmid vector, is advantageous to incorporate a 3'-phosphorothiolate moiety at each terminal end, for example, at each 3' terminal end. An insert acceptor having a 5'-OH at each terminal end can ligate to the plasmid vector to produce an insert-containing vector. The insert-containing vector can therefore contain two or more nicks, one at each junction between the 5'-termini of the vector and 3'-termini of the insert. The insert-containing vector, when transformed into a host cell, such as a strain of *E. coli*, will be repaired to generate a replicatable plasmid.

A vector containing a polynucleotide-3' phosphorothiolate can contain nucleic acids from various organism including, for example, bacteria, bacteriophage, yeast, plants and mammals, as well as nucleic acids from viruses. A vector can contain a variety of features useful for replication, gene expression, cloning and protein expression. For example, promotor, enhancer, poly A sequences, other regulatory sequences, genes encoding various polypeptides and selectable markers can be contained in a vector. A vector containing a polynucleotide-3' phosphorothiolate can be prepared from a variety of vectors well known in the art, such as by incorporation of a 3' phosphorothiolate moiety post-synthetically or during the synthesis of the vector.

The invention provides a polynucleotide 3'-phosphorothiolates, preferably in kit form. A kit contains (a) a polynucleotide-3' phosphorothiolate; and (b) a buffer in an aqueous solution in a suitable packaging material. A polynucleotide 3'-phosphorothiolate can be generated by contacting a polynucleotide 3'-phosphorothiolate precursor with an activator. Therefore, the invention also provides a kit containing a polynucleotide 3'-phosphorothiolate precursor and an activator. A kit of the invention is useful for ligating nucleic acids. A kit includes at least one invention polynucleotide 3'-phosphorothiolate, as a separately packaged chemical reagent(s) in an amount sufficient at least one ligation. As described herein, a polynucleotide 3'-phosphorothiolate can be contained in a variety of nucleic acids, including, for example, a DNA such as a cDNA or genomic DNA, an RNA, such as a mRNA or catalytic RNA, a vector such as a cloning or expression vector, viral DNA or BAC, an oligonucleotide, an insert, a branched polynucleotide, and the like.

For a kit containing oligonucleotide polynucleotide 3'-phosphorothiolates, the kit will generally contain two or more oligonucleotide polynucleotide 3'-phosphorothiolates. When the kit is to be used for generating a PCR product containing a 3'-phosphorothiolate, the kit will contain at least two oligonucleotides, at least one of which is a polynucleotide 3'-phosphorothiolate, that can serve as primers for PCR. Those of skill in the art can readily incorporate invention oligonucleotides in combination with the provided buffer(s) and appropriate solutions for the practice of the invention methods as described herein. A kit containing a polynucleotide 3'-phosphorothiolate contains a buffer that provides the proper conditions for performing a ligation, and can contain control samples known to undergo ligation under appropriate conditions.

The contents of the kit of the invention, for example, a polynucleotide 3'-phosphorothiolate, such as an oligonucleotide or vector polynucleotide 3'-phosphorothiolate and buffer in aqueous solution, are contained in packaging material, preferably to provide a sterile, contaminant-free environment. In addition, the packaging material contains instructions indicating how the materials within the kit can be employed to ligate nucleic acids. The instructions for use typically include a tangible expression describing the reagent concentration or at least one ligation method parameter, such as a time period or temperature of incubation, and the like.

The invention provides a compound of the following formula:

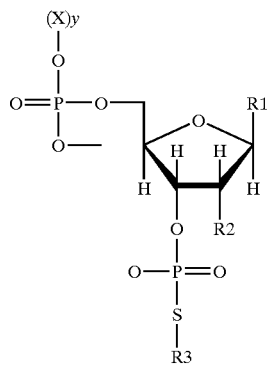

wherein,

X is a nucleotide;

Y is a positive integer;

R1 is a nucleotide base;

R2 is a hydrogen atom or hydroxyl; and

R3 is a halo, alkyl, substituted alkyl, sulfonate moiety, phenyl, substituted phenyl.

The polynucleotide-3' phosphorothiolate compound of the invention can contain a variety of substituents that function as good leaving groups at the R3 position. Substituents that function as good leaving groups are well known to those skilled in the art, and include, for example, alkyl halides, phenyl halides, alkyl sulfonates and phenyl sulfonates.

The polynucleotide-3' phosphorothiolate compound of the invention can be conveniently prepared as described in Example VII, by modifications of the method that produce the polynucleotide-3' phosphorothiolate compound of the invention, and by other methods which can be determined by those skilled in the art. Such modifications of the procedure for preparing a polynucleotide-3'phosphorothiolate can include, for example, the use of alternate solvents, buffers and temperature conditions.

The invention provides another method of ligating a nucleic acid. The method consists of contacting a polynucleotide-5' phosphorothiolate with a non-sequence specific topoisomerase, or a fragment or modification thereof, and an acceptor polynucleotide under conditions that allow formation of a phosphodiester bond between the polynucleotide-5' phosphorothiolate and the acceptor polynucleotide, with the proviso that the polynucleotide-5' phosphorothiolate does not contain the nucleotide sequence G(C/T)CCTT (SEQ ID NO:5).

Like the methods of the invention for non-enzymatic ligation, the methods for topoisomerase-mediated ligation using a polynucleotide-5' phosphorothiolate can be applied to a variety of applications, from molecular cloning to constructing polynucleotides useful for a variety of purposes, such as for detecting an analyte, producing template nucleic acids, generating catalytic molecules such as RNA molecules and RNA-DNA hybrids.

The methods for topoisomerase-mediated ligation using a polynucleotide-5' phosphorothiolate involve covalently trapping a topoisomerase at a 5'-phosphorothiolate moiety of a polynucleotide-5' phosphorothiolate. The trapped topoisomerase enzyme catalyzes the ligation of the polynucleotide-5' phosphorothiolate to any complementary acceptor nucleic acid having a 5'-OH group. As such, a topoisomerase can be covalently bound to a vector or insert to promote ligation to a complementary acceptor nucleic acid within seconds or minutes. A topoisomerase-bound vector can be used to conveniently and efficiently ligate to one, several or many different inserts. Such a vector can be used, for example, for routine cloning of single inserts as well as for constructing polynucleotide libraries. Conversely, a topoisomerase-bound insert can be used to conveniently and efficiently ligate to one, several, or many vectors. Such an insert could be cloned into a panel of vectors, for example, when it is desired to test multiple vectors having different functional properties for a particular application, such as gene or protein expression.

Topoisomerase I enzymes are capable of cleaving duplex polynucleotides at sites that contain a 5' bridging phosphorothiolate moiety and have been used as suicide substrates for recombinases and topoisomerases (Burgin et al. *Nucleic Acids Research,* 23:15, 2973–2979, (1995); Burgin et al. *Current Biology,* 5:1312–1321, (1995); Redinbo et al. *Science,* 279:1504–1513 (1998)). Upon cleavage of such a site, topoisomerase I becomes covalently attached to the 3' end of the broken strand through a phosphotyrosine bond between a catalytic tyrosine in the active site of topoisomerase I and the 3' end of the broken strand. This generates a 5' sulfhydryl leaving strand instead of a 5'-OH, which is not a sufficient nucleophile to reverse the cleavage reaction. Thus, cleavage by topoisomerase I at a 5'-bridging phosphorothiolate is irreversible in the absence of an acceptor polynucleotide. The methods of the invention employ 5'-bridging phosphorothiolates to trap topoisomerase I in a covalent complex with a polynucleotide to generate a complex that can perform a ligation reaction with an acceptor polynucleotide having a 5'-OH.

In the present invention, polynucleotide 5'-phosphorothiolates are now used for promoting topoisomerase-mediated ligation of nucleic acids. A non-sequence specific topoisomerase is targeted to a specific nucleic acid sequence by incorporating a 5'-bridging phosphorothiolate at a desired site within the sequence. A non-sequence specific topoisomerase can promote ligation between the topoisomerase-bound polynucleotide and an acceptor polynucleotide. The topoisomerase first cleavages at the 5'-phosphorothiolate moiety in the scissile (top) strand of a duplex polynucleotide. The topoisomerase then catalyzes the attack of the 5'-OH of the acceptor nucleic acid on the topoisomerase-bound polynucleotide 5-phosphorothiolate to form a phosphodiester bond, displacing the enzyme.

A topoisomerase can cleave at a 5' phosphorothiolate moiety at any location within a scissile polynucleotide strand, allowing that the 5' phosphorothiolate moiety is flanked by at least several bases on the 5' side, and at least one base on the 3' side. Cleavage at a 5' phosphorothiolate moiety by a topoisomerase will generate a single stranded fragment if the cleavage site is near the terminal end of a linear substrate and produce a 5' overhang on the bottom strand. The single stranded fragment, if relatively small, such as about 20 or fewer bases, 10 or fewer bases, 6 or fewer bases, 4 or fewer bases, or 2 or fewer bases, will dissociate from the duplex to produce the overhang. A larger fragment that is not spontaneously dissociated from a duplex can be dissociated, for example, by heating to 80° C., followed by quick cooling and separation of the fragment, such as by gel purification, affinity isolation or other methods well known in the art. Therefore, an overhang generated by cleavage by a topoisomerase can contain contain few bases or many bases, depending on the site to which the topoisomerase is targeted.

Therefore, a user of the methods of the invention for topoisomerase-mediated ligation of nucleic acids can design polynucleotide 5' phosphorothiolates having a diverse array of different overhangs. The variety of different overhangs are useful for ligating diverse acceptor polynucleotides and for cloning using desired restriction sites, and particularly for uni-directional cloning, in which an insert is ligated into a vector in a specific orientation, as dictated by the complementarity of 3'- and 5'-terminal ends of the insert and vector.

A non-sequence specific topoisomerase can be, for example, a eukaryotic or viral topoisomerase, such as a human topoisomerase I. An exemplary human topoisomerase termed Topo65 is provided herein. Topo65 is a topoisomerase fragment having topoisomerase activity, that provides several advantages over a native topoisomerase. For example, Topo65 can be conveniently purified in large quantity by metal ion affinity chromatography, it expressed in higher amount than native topoisomerase, for example, in insect cells, and is comparatively more stable than native topoisomerase.

The invention provides an isolated non-sequence specific topoisomerase, or a fragment or modification thereof having topoisomerase activity. An isolated topoisomerase can be prepared by a variety of methods well-known in the art, for example, by recombinant expression Systems described herein, and biochemical methods of purification such as precipitation and chromatographic methods. A non-sequence specific topoisomerase of the invention can be prepared, for example, by recombinant expression in any compatible vector/host system. A variety of protein expression systems are well known in the art and include, for example, prokaryotic and eukaryotic expression systems. Prokaryotic expression systems are advantageous due to their ease in manipulation, low complexity growth media, low cost of growth media, rapid growth rates and relatively high yields. Well known prokaryotic expression systems include, for example, E. coli bacterial expression systems based on bacteriophage T7 RNA polymerase, the trc promotor, the araB promotor and bacillus expression. Eukaryotic expression systems are advantageous because expressed polypeptides can contain eukaryotic post-translational modifications such as O-linked glycosylation, phosphorylation and acetylation and can have improved protein folding. Well known eukaryotic expression systems include, for example, expression in yeast, such as *Pichia pastoris* and *Pichia methanolica*, expression in insect systems such as the *Drosophila* S2 system and baculovirus expression systems and expression in mammalian cells using adenoviral vectors and cytomegalovirus promotor-containing vectors. Described herein is the purification of Topo65 from sf9 insect cells infected with baculovirus encoding Topo65 (see Example IV).

A non-sequence specific topoisomerase of the invention can be purified using a variety of methods of protein purification well known in the art. Biochemical purification can include, for example, steps such as solubilization of the topoisomerase-expressing cell, isolation of the desired subcellular fractions, chromatography, such as ion exchange, size, or affinity-based chromatographies, electrophoresis, and immunoaffinity procedures. Other well-known methods are described in Deutscher et al., Guide to Protein Purification: Methods in Enzymology Vol. 182, (Academic Press, (1990)). The methods and conditions for biochemical purification of a polypeptide of the invention can be chosen by those skilled in the art, and the purification monitored, for example, by staining SDS-PAGE gels containing protein samples, by immunodetection methods such as Western blotting and ELISA, and by functional assay of topoisomerase activity.

A topoisomerase can be modified, for example, to increase polypeptide stability, alter a topoisomerase activity, facilitate detection or purification, or render the enzyme better suited for a particular application, such as by altering substrate specificity. Computer programs known in the art can be used to determine which amino acid residues of a topoisomerase can be modified as described above without abolishing a topoisomerase activity (see, for example, Eroshkin et al., *Comput. Appl. Biosci.* 9:491–497 (1993)). In addition, structural and sequence information can be used to determine the amino acid residues important for topoisomerase activity. For example, a topoisomerase crystal structure (Redinbo et al., supra) and comparisons of topoisomerase amino acid sequences, such as that shown for poxyirus topoisomerases in Krogh et al. (*Virology,* 264, 441–451 (1999)) can provide guidance in determining amino acid residues that can be altered without abolishing topoisomerase activity.

The invention provides another kit. The kit consists of (a) a polynucleotide-5' phosphorothiolate, with the proviso that the polynucleotide-5' phosphorothiolate does not contain a nucleotide sequence selected from the group of SEQ ID NO:5, SEQ ID NO:6 or SEQ ID NO:7; (b) a non-sequence specific topoisomerase, or fragment or modification thereof having topoisomerase activity; and (c) a buffer in an aqueous solution.

A kit of the invention is useful for generating a covalent complex of Topo65 and a polynucleotide and for ligating nucleic acids. A kit includes at least one invention polynucleotide-5' phosphorothiolate, with the proviso that the polynucleotide-5' phosphorothiolate does not contain a nucleotide sequence selected from the group of SEQ ID NO:5, SEQ ID NO:6 or SEQ ID NO:7 and a non-sequence specific topoisomerase of the invention as a separately packaged chemical reagent(s) in an amount sufficient at least one ligation. For a kit containing oligonucleotide polynucleotide 5'-phosphorothiolates, the kit will generally contain two or more oligonucleotide polynucleotide 5'-phosphorothiolates. When the kit is to be used for generating a PCR product containing a 5'-phosphorothiolate, the kit will contain at least two oligonucleotide polynucleotide 5'-phosphorothiolates that can serve as primers for PCR. Oligonucleotide polynucleotide 5'-phosphorothiolates of the kit can contain a variety of useful sequences. For example, an oligonucleotide can contain a restriction site and the sequence of a vector from which a polynucleotide is amplified. Those of skill in the art can readily incorporate invention oligonucleotides in combination with the provided non-sequence specific topoisomerase and buffer(s) and other appropriate solutions for the practice of the invention methods as described herein.

A polynucleotide 5'-phosphorothiolate can have a variety of chemical, structural and function properties, as desribed above. A polynucleotide 5'-phosphorothiolate can be prepared using a variety of methods, also described above. Thus, a variety of polynucleotide 5'-phosphorothiolates can be provided in a kit of the invention. An exemplary polynucleotide 5'-phosphorothiolate that can be contained in a kit is an oligonucleotide containing a 5'-phosphorothiolate moiety. The oligonucleotide could be used with another oligonucleotide to amplify a PCR product, such as a vector or insert, containing a 5'-phosphorothiolate. A polynucleotide 5'-phosphorothiolate PCR product can then be covalently bound to the kit-provided Topo65 to generate a topoisomerase-polynucleotide 5'-phosphorothiolate complex capable of ligating to a complementary acceptor polynucleotides. A 5'-phosphorothiolate oligonucleotide can also be used, for example, to amplify a plurality of different polynucleotides. The resulting population of PCR products can then be bound to a topoisomerase and ligated, for example, to an acceptor nucleic acid, such as a vector. For convenience, a kit can also contain vectors that can optionally be used with the Topo65 and polynucleotide 5'-phosphorothiolates of the invention.

An acceptor vector or 5'-phosphorothiolate-containing vector can contain a variety of terminal ends, including for example, 5' or 3' terminal overhangs having nucleic acid sequences complementary to terminal end overhangs generated by a restriction endonuclease, such as a HindIII, EcoRI, BamHI or BstBI overhang. A vector bound to a Topo65 through a 5'-phosphorothiolate moiety, or capable of binding Topo65 through a $5^1$-phosphorothiolate moiety, can contain two like or different terminal overhangs. Two different overhangs can correspond to overhangs generated by two restriction enzymes. A topoisomerase-bound vector containing overhangs corresponding to two different restriction enzyme overhangs can conveniently be used for rapid cloning of inserts having the corresponding overhangs. For example, a topoisomerase-bound vector can contain BamHI and EcoRI overhangs for cloning insert acceptor polynucleotides generated by cleavage with BamHI and EcoRI.

A kit containing a polynucleotide 5'-phosphorothiolate and Topo65 enzyme also contains a buffer that provides the proper conditions for performing a non-sequence specific topoisomerase-mediated ligation, and can contain control samples known to undergo ligation under appropriate conditions.

The invention further provides a composition containing (a) a polynucleotide-5' phosphorothiolate, with the proviso that the polynucleotide-5' phosphorothiolate does not contain a nucleotide sequence selected from the group of SEQ ID NO:5, SEQ ID NO:6 or SEQ ID NO:7; and (b) a non-sequence specific topoisomerase, or fragment or modification thereof having topoisomerase activity.

The invention also provides a compound of the formula:

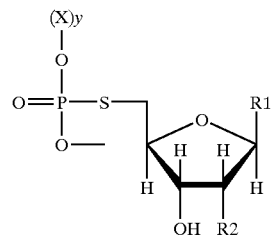

wherein,
X is a nucleotide;
Y is a positive integer;
R1 is cytosine or guanine; and
R2 is a hydrogen atom or hydroxyl.

The polynucleotide 5'-phosphorothiolate compound of the invention, such as a 5'-S-dimethoxytrityl-3'-O-cyanoethyl-NN-diisopropyl-phosphoramidite-2'-deoxy-N-benzoyl-cytosine or 5'-S-dimethoxytrityl-3'-O-cyanoethyl-NN-diisopropyl-phosphoramidite-2'-deoxy-N-isobutyryl guanosine can be conveniently prepared as described in Example VI and FIG. 7, by modifications of the method that produce the polynucleotide-3' phosphorothiolate compound of the invention, and by other methods which can be determined by those skilled in the art. Other 5'-phosphorothiolate compounds useful in the methods of the invention, such as those based on uridine and thymidine can be prepared, for example, as described in Mag et al., *Nucleic Acids Res.*, 19(7):1437–41 (1991).

The methods of the invention involve ligating polynucleotides, such as DNA and RNA. Both DNA and RNA molecules can be obtained using a variety of methods well known in the art. These molecules can be obtained by purification from a natural source, such as a cell from an organism, by purification from a host cell, such as a cell which overexpresses a plasmid DNA, and by chemical synthesis, such as automated oligonucleotide synthesis methods well known in the art.

The methods of the invention involve transforming a vector into a host cell. Methods for introducing a vector into a host cell are well known in the art and include, for example, various methods of transformation such as calcium chloride and electroporation and transfection such as calcium phosphate, DEAE-dextran and liposome mediated methods, viral transduction, electroporation.

The methods of the invention involve preparing duplex polynucleotides such as duplex oligonucleotides. A variety of methods for preparation of duplex polynucleotides are well known in the art. An exemplary method by which duplex oligonucleotides and polynucleotides can be prepared is by mixing equimolar concentrations of complementary strands, each at a final concentration of about 0.1 mM, in the presence of a salt, such as 6 M NaCl, and then heating to 80° C. followed by cooling to room temperature over a period of 8 hours.

It is understood that modifications which do not substantially affect the activity of the various embodiments of this invention are also included within the definition of the invention provided herein. Accordingly, the following examples are intended to illustrate but not limit the present invention.

EXAMPLE I

Nonenzymatic Ligation of Nucleic Acid

This example shows that a polynucleotide 3'-phosphorothiolate can be ligated to an acceptor polynucleotide.

A polynucleotide 3-phosphorothiolate mediates non-enzymatic ligation through a mechanism analogous to that of a topoisomerase. Topoisomerase-mediated ligation is effective because the 3'-phosphotyrosine is a relatively high energy intermediate and therefore labile; formation of a 5'-3' DNA phosphodiester bond is extremely stable and energetically favored. Topoisomerases require no external energy source (e.g. ATP) to catalyze the cleavage and ligation reactions. It was hypothesized that other chemically modified 3'-phosphodiesters could mimic this labile intermediate. To test this hypothesis an oligonucleotide containing a 3'-S-(paranitrophenyl) moiety (termed 3'-SNP) was prepared. This compound contains a substitution of a sulfur for an oxygen because sulfur-phosphorous bonds are significantly more labile than oxygen-phosphorous bonds and therefore provides a better leaving group. In addition, the pKa of a thiol is three orders of magnitude lower than an alcohol, and the 4-nitro functional group reduces the pKa of the thiol even further, creating a very labile 3-phosphorothiol ester. The 3'-SNP was predicted to be a good leaving group during a ligation reaction in which the acceptor polynucleotide supplies the 5'-OH necessary to displace the 4-nitrothiobenzene. This reaction is depicted in FIG. 1. Other thioesters and labile phophoesters can function as leaving groups in the non-enzymatic ligation reactions described herein. As shown below, a 3'-SNP within a polynucleotide served as a good leaving group, allowing a polynucleotide containing a 3'-SNP to undergo non-enzymatic ligation with an acceptor nucleic acid.

Figure 2:
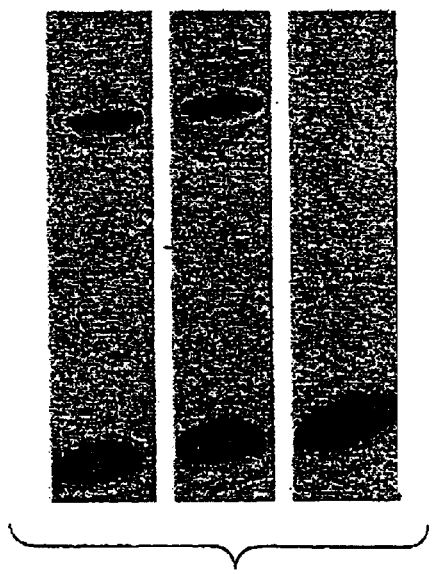
FIG. 2 is a photograph of a denaturing polyacrylamide gel which shows the product of ligating a duplex 3'-phosphorothiolate polynucleotide and an acceptor oligonucleotide.

To determine if a polynucleotide having a 3'-SNP moiety could act as a leaving group during a ligation reaction and form a phosphodiester bond with another nucleic acid molecule in the absence of any enzyme, a 3'-SNP-moiety was incorporated at a nick in a duplex polynucleotide. The 3'-SNP-containing polynucleotide was radioactively labeled at the 5' end and was incubated for 3 hours in the presence of an acceptor oligonucleotide. The reaction mixtures were then separated on a denaturing polyacrylamide gel. FIG. 2 is an autoradiograph which shows the products generated when a 3'-SNP-containing duplex DNA is incubated with a 20-mer acceptor oligonucleotide (lane 1), a mixture of 20-mer and 24-mer acceptor oligonucleotides (lane 2) or in the absence of acceptor oligonucleotide (lane 3). The expected ligation products were observed, demonstrating that ligation can occur in the absence of any enzymes.

EXAMPLE II

Covalent Bond Formation Between Topo65 and 5'-Phosphorothiolate-Containing Polynucleotides This example shows that Topo65 can cleave a duplex DNA molecule containing a 5'-phosphorothiolate moiety located two or four base pairs upstream from a blunt end.

To determine if Topo65, a recombinant form of human topoisomerase I, described in detail below, can cleave near the end of a duplex DNA molecule, Topo65 was incubated with oligonucleotide substrates containing 5'-phosphorothiolate moieties located two or four base pairs upstream from a blunt end. The duplex substrates contained nucleic acid sequences at their 3' end that, when cleaved by Topo65, would generate 2 and 4 base overhangs compatible with terminal end overhangs generated by the restriction enzymes BstBI and BamHI, respectively. The substrates contained a 5'-EcoRI overhang on the other end of the duplex oligonucleotide so that the duplex oligonucleotides could be ligated, using standard T4 DNA ligase, onto linear plasmid molecules.

FIGS. 3A and 3B shows duplex substrates containing a 5'-bridging phosphorothiolate "OPS" moiety located 4 or 2 base pairs from the 3' ends of a scissile strand (top strand) which is annealed to a complementary strand (bottom strand) having a 5' dimethoxytrityl group (DMT) to form a duplex having a 5' EcoRI overhang (left ends). Topo65 cleavage of the duplex results in Topo65 being trapped at the OPS moiety topo cleavage site. The site of topoisomerase trapping is depicted by an arrow in FIGS. 3A and 3B. Subsequent cleavage of the scissile strand of the duplex to which Topo65 is covalently bound generates a 4 or 2 base 5' overhang which is complementary to the 5' overhangs generated by restriction digestion with the enzymes BamHI (4 base overhang) or BstBI (2 base overhang).

FIG. 3A shows the nucleotide sequences of the oligonucleotides contained in duplex oligonucleotide pair TCRIBamS/AS. The nucleotide sequences are as follows: TCRIBamS: 5' AATTCGCGGCCGCAAAAAGACTTGATC 3' (SEQ ID NO:8) and TCRIBamAS: 5' GATCAAGTCTTTTTGCGGCCGCG (SEQ ID NO:9). FIG. 3B shows the nucleotide sequences of the oligonucleotides contained in duplex oligonucleotide pair TCRBstBS/AS. The nucleotide sequences are as follows: TCRBstBS: 5' AATTCGCGGCCGCAAAAAGACTTCG (SEQ ID NO:10) and TCRBstIBAS: 5'CGAAGTCTTTTTGCGGCCGCG (SEQ ID NO:11).

The oligonucleotides TCRIBamS and TCRIBstBS (S oligonucleotides) were reverse-phase purified and had their DMT protective group removed prior to use. The AS oligonucleotides were purified by reverse-phase, but 5' DMT groups were not removed. For each oligonucleotide pair, the sense (S) and antisense (AS) oligonucleotides were titrated against one another and, on the basis of these experiments, a 1:1 ratio (wt:wt) of S:AS oligonucleotides, for each oligonucleotide pair, was used to generate duplex substrate for reaction with Topo65.

Figure 4:
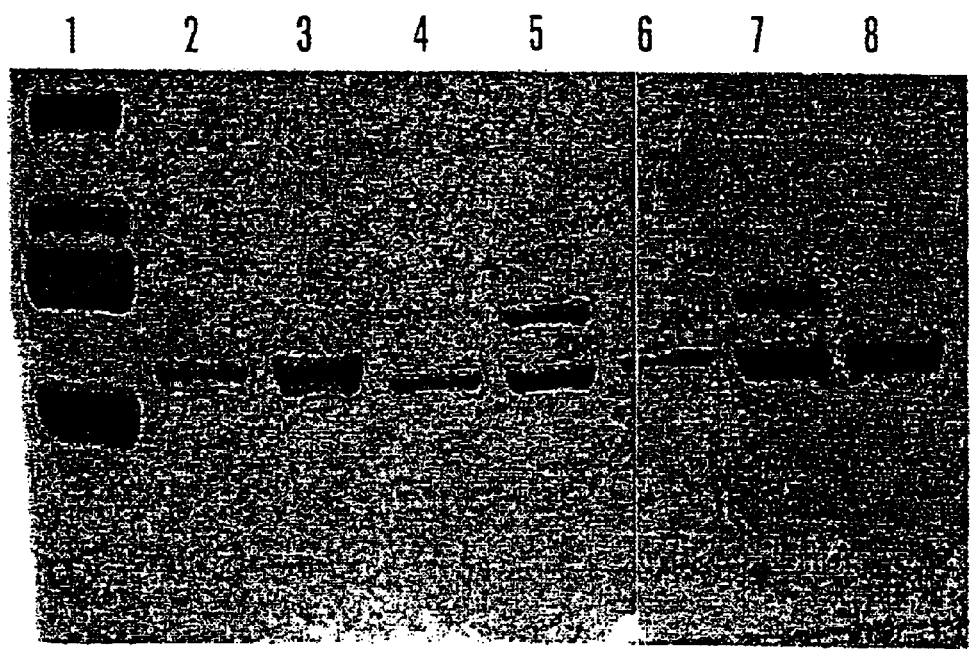
FIG. 4 is a photograph of a polyacrylamide gel which shows that Topo65 forms a covalent complex with oligonucleotide substrates.

The duplex substrates shown in FIGS. 3A and 3B were reacted overnight at room temperature with Topo65. The reaction mixtures contained 3 $\mu$M Topo65, 10 $\mu$M duplex substrate, 10 mM Tris-HCl, pH 7.5, 100 mM KCl, 10 mM MgCl2, 1 mM EDTA, and 2 mM DTT. The reaction products were adjusted to 1 M NaCl or NOT and then analyzed by 10% SDS-PAGE and Coomassie Blue staining (lanes 4–7). FIG. 4 is a photograph of the stained gel.

As a control, Topo65 was allowed to react with a duplex 22-mer suicide substrate. The suicide substrate contains a centrally positioned 5'-bridging phosphorothiolate. The sequences of the 22-mer oligonucleotides contained in the suicide substrate 22-mer duplex are (top strand) 5' AAAAAGACTTAGAAAAATTTTT 3' (SEQ ID NO:18 and (bottom strand) 5' AAAAATTTTTCTAAGTCTTTTT (SEQ ID NO:19). The position of the 5'-briding phosphorothiolate incorporated into the top oligonucleotide strand is between the sequences GACTT and AGAAAA. Topo65 quantitatively reacts with this suicide substrate, demonstrating that all of the enzyme is functional for cleavage.

Samples contained in each lane of the gel shown in FIG. 4 are as follows: 1) Molecular weight markers; 2) Topo65 reacted with suicide 22mer with salt; 3) Topo65 reacted with suicide 22-mer without salt; 4) Topo65 reacted with TCRIBamS/AS with salt; 5) Topo65 reacted with TCRIBamS/AS without salt; 6) Topo65 reacted with TCRIBstBS/AS with salt; 7) Topo65 reacted with TCRIBstBS/AS without salt; and 8) Topo65, 2 $\mu$g.

Approximately 20% of the Topo65 can be trapped with SDS in covalent complex with DNA after cleavage of the TCRIBamAS/TCRIBamS or TCRIBstBS/TCRIBstBAS substrates. The SDS-PAGE gel revealed a shift in the mobility of Topo65 when it is reacted with both TCRIBamS/AS and TCRIBstBS/AS, indicating that Topo65 can react at a cleavage site 2 to 4 base pairs from the 3' end of a duplex DNA. The mobility shift is equivalent to about 15 kDa, which is the expected molecular weight for a 22-mer attached to Topo65.

This experiment was repeated after removal of the DMT from the AS oligonucleotides by acid treatment, and an identical gel-shift was observed on reaction of "DMT off" oligonucleotide complexes with Topo65. However, no gel shift was observed if duplex generated from ratios of single strand oligonucleotides alone, for example, TCRIBamS, TCRIBamAS, TCRIBstBS or TCRIBstBAS alone.

These results indicate that Topo65 cleaved at a 5'-phosphorothiolate moiety located two or four base pairs upstream from a blunt end.

EXAMPLE III

Topo65 Mediated Ligation of Oligonucleotide Substrates

This example shows Topo65 mediated ligation of oligonucleotide substrates following cleavage at the 5'-bridging phosphorothiolate located near the end of a DNA duplex.

Figure 5A:
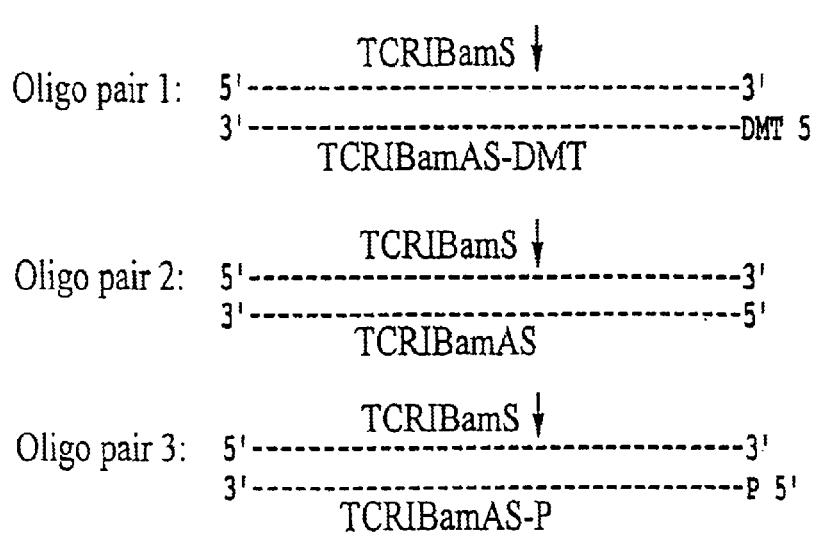
FIG. 5A is a schematic representation of substrate oligonucleotide pairs that contain 5' phosphorothiolate moieties.
Figure 5B:
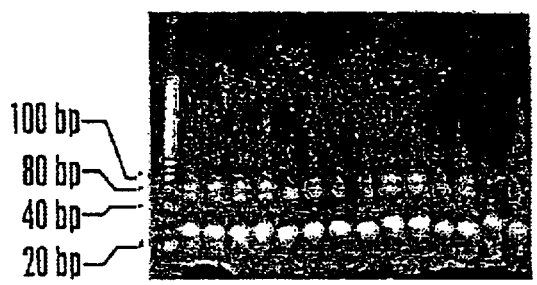
FIG. 5B is a photograph of a polyacrylamide gel which shows products of Topo65-mediated ligation of 5' phosphorothiolate oligonucleotides.
Figure 5C:
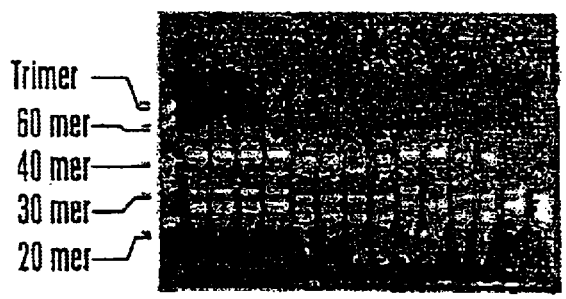
FIG. 5C is a photograph of an denaturing polyacrylamide gel which shows products of Topo65-mediated ligation of 5' phosphorothiolate oligonucleotides.

The SDS-PAGE analysis depicted in FIG. 4 demonstrates that topo I is capable of reacting with the oligo duplex substrates. In order to determine the fate of the substrates themselves, the duplex oligonucleotide substrates shown in FIG. 5A were reacted with Topo65 and the oligonucleotide reaction products were examined by both native and denaturing PAGE (FIGS. 5A and 5B, respectively). Through this analysis, the efficient Topo65-mediated generation of dimeric (about 50 bp) and even trimeric (about 70 bp) DNA molecules was observed (FIG. 5B, lanes 4 and 5).

FIG. 5A depicts oligonucleotide substrates reacted with Topo65, labeled as Oligo pairs 1 through 6. Oligonucleotide substrates (pairs 1 to 3) were reacted with Topo65, adjusted to 500 mM NaCl or NOT, and the resulting mixtures were digested with proteinase K in SDS prior to analysis by native PAGE (FIG. 5B) or denaturing PAGE with urea (FIG. 6B). Unreacted control oligonucleotide duplex samples are shown in lanes 14 and 15. Each gel contained the following samples: (1) 20 bp DNA ladder, (2) oligonucleotide pair 1 with salt, (3), oligonucleotide pair 1 without salt, (4) oligonucleotide pair 2 with salt, (5) oligonucleotide pair 2 without salt, (6) oligonucleotide pair 4 with salt, (7) oligonucleotide pair 4 without salt, (8) oligonucleotide pair 5 with salt, (9) oligonucleotide pair 5 without salt, (10) oligonucleotide pair 3 with salt, (11) oligonucleotide pair 3 without salt, (12) oligonucleotide pair 6 with salt, (13) oligonucleotide pair 6 without salt, (14) 400 ng unreacted oligo pair 1, (15) 400 ng unreacted oligo pair 4.

Annealed "DMT ON" and "DMT OFF" oligo duplexes were reacted with Topo65 as described above. After overnight reaction at room temperature, SM NaCl was added to a final concentration of 600 mM and reaction continued for a further 2–3 hours at room temperature. Salt shifts the cleavage:ligation equilibrium of the top65 reaction towards ligation. The presence of 600 mM NaCl thus results in an increased concentration of the DNA species produced by Topo65-mediated cleavage and relegation of duplex substrates TCRIBamS/AS and TCRIBstBS/AS. The reaction was stopped with 0.1% SDS and then digested with proteinase-K (PK), for 30 minutes at 37 degrees, to remove the Topo65 protein. DNA product was analyzed on denaturing and native acrylamide gels. In all cases, DNA products of about 50 bp and about 70 bp were generated on reaction of Topo65 with TCRIBamS/AS (27mer:23mer) and TCRIBstBAS/AS (25mer:21mer). There were no differences in either size or quantity of the products generated using "DMT OFF" vs "DMT ON" oligo duplexes. The products observed using TCRIBstBS/AS as substrate were consistently several base pairs smaller than those obtained with TCRIBamS/AS as substrate.

It should be noted that the Oligo pairs 1 and 3 were thought to contain DMT or phosphate blocking groups on the 5' end of each AS strand. The presence of such groups should have blocked topo I-mediated ligation events. However, the observed lack of expected blocking is attributed to the apparent absence of 5' DMT or phosphate groups on the AS oligos, as determined by HPLC analysis). Hence, all three oligo pairs shown in FIG. 5A were capable of being cleaved by Topo65 at the 5' bridging phosphorothiolate moiety, and thenligated by Topo65 to a second oligo pair to generate a dimeric 50-mer.

Cloning and Sequence Analysis of the 50-mer Topo I Ligation Product

The dimeric oligos of about 50 base pairs resulting from Topo65 activity were gel purified. DNA ligase was used to clone these fragments into an EcoRI digested plasmid vector. Sequence analysis of clones containing an insert demonstrated that in each case, Topo65 successfully ligated two oligonucleotides head to head. This is consistent with the predicted product of Topo65 cleavage at the 5' phosphorothiolate moiety followed by ligation of the 5' end of the AS strand to the 3' end of the Topo65 cleaved 5' strand.

Once Topo65 has formed a covalent complex by cleaving a 5' phosphorothiolate-containing substrate, the activated complex can ligate directly to a blunt end of a second unreacted duplex, or can react with another covalent Topo65-oligonucleotide complex. The present assay does not discern between these two possibilities.

In both the case of the TCRIBamS/AS duplex and the TCRIBstBS/AS duplex, the sequence of the 50 mer product that is generated on reaction with Topo65 is that which is expected if cleavage and re-ligation occurs at the phosphorothiolate moiety. FIG. 3C depicts the TCRIBamS/AS duplex after Topo65 cleavage. The GATC sequence removed on Topo65 cleavage yields a BamHI compatible 5' overhang. The sequence of the expected ligation product if two cleaved molecules are ligated at GATC overhang is shown in FIG. 3D. This sequence is identical to the experimentally determined sequence of the product of topo-mediated ligation of the TCRIBamS/AS duplex cloned into EcoRI sites of vector and sequenced using T3 and T7 primers. This sequencing data indicates that Topo65 cleaves the duplexes TCRIBamS/AS and TCRIBstBAS at the 5' phosphorothiolate topo cleavage site to leave a 5' GATC or 5' GC overhang respectively.

The Topo65-mediated oligonucleotide linkage reaction with both BamHI (4 bases from the end) and BstBI (2 bases from the end) sequences indicates that this human topoisomerase I-mediated ligation event can be achieved with more than one sequence, in contrast to Vaccinia virus topoisomerase. Since it is well established that DNA ligase can not ligate a 5' OH to a 3' phosphate, the dimeric oligos which were cloned and subsequently sequenced could only have resulted from the activity of Topo65.

EXAMPLE IV

Topo65 Mediated Circularization of 5'-Phosphorothiolate-Containing Plasmid DNA

This example shows that Topo65 can mediate circularization of linear plasmid DNA that has been adapted at both ends with oligonucleotide duplexes that contain a 5'-briding phosphorothiolate near the 5' end of the scissile strand.

To further examine the ability of Topo65 to mediate ligation of DNAs containing 5'-briding phosphorothiolate near the 5' end of the scissile strand, a vector was adapted with duplex oligonucleotides TCRIBamS/AS described in Example II. FIG. 6A depicts the linearized and oligonucleotide adapted vectors. T4 DNA ligase was then used to adapt the vector ends with TCRIBamS oligonucleotide and TCRIBamAS oligonucleotides that contained or lacked a 5' phosphate. EcoRI-digested vector was incubated at 16° C. overnight with a 300-fold molar excess of oligonucleotides. The adapted vector was then incubated in the presence or absence of Topo65 in 10-fold molar excess, overnight at room temperature in a reaction buffer containing 10 mM Tris-HCl, pH 7.5, 100 mM KCl, 10 mM MgCl2, 1 mM EDTA and 2 mM DTT. After this incubation, 5 M NaCl was added to obtain a final concentration of 600 mM, and the mixture remained at room temperature for three hours. To this mixture, SDS was added to a final concentration of 0.1%, Proteinase-K was added to a final concentration of 100 μg/ml, and the mixture was incubated at 37° C. for 30 minutes. The DNA was isolated by phenol/chloroform extraction, followed by ethanol precipitation. The isolated DNA was used to transform TOP10F' cells, which were then plated onto 2YT/Ampicillin agar.

The inserts obtained from 3–6 clones from each plate were sequenced and found to contain the head to head ligated oligonucleotides as predicted if Topo65 cleaves at the 5' phosphorothiolate moiety and then mediates ligation to an acceptor polynucleotide.

As depicted in FIG. 6B, under conditions in which adaptored vector containing TCRIBamS and TCRIBamAS lacking a 5'-phosphate was incubated with Topo65, 4 of 6 clones were self-ligated adaptored PKSII and 2 of 6 clones had no insert. Under conditions in which adaptored vector containing TCRIBamS and TCRIBamAS having a 5'-phosphate was incubated with Topo65, 2 of 6 clones were self-ligated adaptored pKSII and 1 of 6 clones had no insert, and 3 of 6 clones were re-circularized adaptored vector with deletion. Under conditions in which adaptored vector containing TCRIBamS and TCRIBamAS lacking a 5'-phosphate was incubated in the absence of Topo65, 1 of 3 clones were re-circularized adaptored vector containing one adaptor, 1 of 3 clones were re-circularized adaptored vector with deletion, and 1 of 3 clones had no insert.

EXAMPLE V

Purification of Topo65

This example shows a method of purifying Topo65 from baculovirus-infected sf9 insect cells.

Topo65 was prepared by infecting Sf9 insect cells grown to about 2×10⁶ cells/ml with a baculovirus containing a vector encoding Topo65 (Ac Topo65 viral stock passage 2). Insect cells were harvested 60 hours after infection by centrifugation at 1500 rpm for 5 minutes at 4° C. Cells were then washed by combining cells in ~500 ml PBS at 4° C. and collected by centrifugation at 1500 rpm for 5 minutes at 4° C. Topo65-expressing cells were then lysed by resuspending washed cells in 200 ml lysis buffer (50 mM KCl, 10 mM Tris-HCl, pH 7.5, 2 mM MgCl2, 1% Triton X-100, 0.15 mg/ml PMSF, and 15 mM beta-mercaptoethanol). Nuclei were collected by centrifugation at 2000 rpm for 5 minutes at 4° C. Cytoplasmic supernatant was decanted. Collected nuclei were resuspended in 200 ml resuspension buffer (50 mM KCl, 10 mM Tris-HCl, pH 7.5, 2 mM MgCl2, 0.15 mg/ml PMSF, and 15 mM beta-mercaptoethanol) and then centrifuged at 2000 rpm for 5 minutes at 4° C. Buffer was then removed, and nuclei were washed a second time.

Washed nuclei were resuspended in 40 ml resuspension buffer containing fresh PMSF and beta-mercaptoethanol containing 0.8 ml 0.5M EDTA. Nuclei were then lysed by addition of 45 ml 2X nuclear lysis buffer (80 mM Tris-HCl, pH 7.5, 2 M NaCl, 20% glycerol, 2 mM EDTA) followed by shaking of mixture. DNA was precipitated from the mixture by dropwise addition 50 ml PEG solution (18% PEG-8000, 1 M NaCl, 10% Glycerol) to mixture stirring at 4° C. The mixture was then allowed to stir at 4° C. for 5 hours.

To remove precipitated DNA from the nuclei mixture, centrifugation was performed at 8000 rpm for 10 minutes at 4° C., followed by removal of supernatant. The PEG supernatant was dialyzed against 4 liters dialysis buffer (250 mM KPO4, 1 mM EDTA, 0.1 mM PMSF, and 5 mM beta-mercaptoethanol) overnight at 4° C. To clarify dialyzed PEG supernatant, centrifugation at was performed at 8000 rpm for 20 minutes at 4° C. Topo65 was purified from clarified PEG supernatant by phenyl sepharose chromatography. A column (approximately 10 cm) was packed with Phenyl Sepharose CL-4B (Pharmacia cat. # 17-0810-01, Pharmacia, Piscataway, N.J.) and equilibrated with dialysis buffer. Clarified PEG supernatant was loaded onto a phenyl sepharose column by gravity and fractions were collected on ice. The phenyl sepharose flow through (~200 ml) was diluted with 200 ml of POROS HS buffer A (10 mM Tris-HCl, pH 7.5, 1 mM EDTA, 5 mM beta-mercaptoethanol, 0.1 mM PMSF).

POROS 20 HS Chromatography (Perseptive Biosystems matrix, cat. # 1-3329-06) chromatography (3.32 ml) was performed on Phenyl Sepharose flow through. The column was washed with buffer B (POROS HS buffer A plus 1 M KCl)and then equilibrated column with Buffer A. The phenyl sepharose flowthrough over the equilibrated column at a rate of 2 ml/minute. When all flowthrough was been passed over the column, re-equilibration was performed with 4 column volumes of Buffer A. Protein was eluted from the column with a 15–800 mM KCl gradient. SDS-PAGE was performed using 5–10 ul aliquots of each fraction collected. Fractions containing Topo65 protein (fractions 25-30) were pooled. Topo65 was further purified by MonoQ chromatography of pooled fractions from POROS 20 column. Pooled fractions were diluted with 2 volumes of water and loaded onto a MonoQ column equilibrated with MonoQ Buffer A (25 mM KPO4, pH 7.4, 1 mM EDTA, 1 mM beta-mercaptoethanol, 1 mM PMSF), followed by elution with MonoQ buffer B (1 M KPO4, pH 7.4, 1 mM EDTA, 1 mM beta-mercaptoethanol, 1 mM PMSF).

Further purification of Topo65 was performed by MonoS Chromatography on a MonoS column equilibrated with MonoS buffer A (25 mM KPO4, pH 7.4, 1 mM EDTA, 1 mM beta-mercaptoethanol, 1 mM PMSF). Pooled Topo65 eluate from MonoQ chromatography was loaded onto a MonoS column followed by elution with a 7.5–40% gradient of MonoS buffer B (1 M KPO4, pH 7.4, 1 mM EDTA, 1 mM beta-mercaptoethanol, 1 mM PMSF) over 20 column volumes. SDS-PAGE was performed to detect Topo65 and fractions containing Topo65 protein (fractions 9–13) were pooled. Pooled Fractions from MonoS chromatography were dialyzed overnight against final dialysis buffer at 4° C. (10 mM Tris-HCL, pH 7.5, 1 mM EDTA, and 1 mM DTT). The final concentration of dialyzed material was adjusted to 5 mM DTT and Topo65 concentration was determined by Bradford Assay. The procedure yielded 6 ml of Topo65 at a concentration of 2 mg/ml.

EXAMPLE VI

Synthesis of Polynucleotide-5' Phosphorothiolates

This example describes the synthesis of two polynucleotide 5'-phosphorothiolates.

Figure 7A:
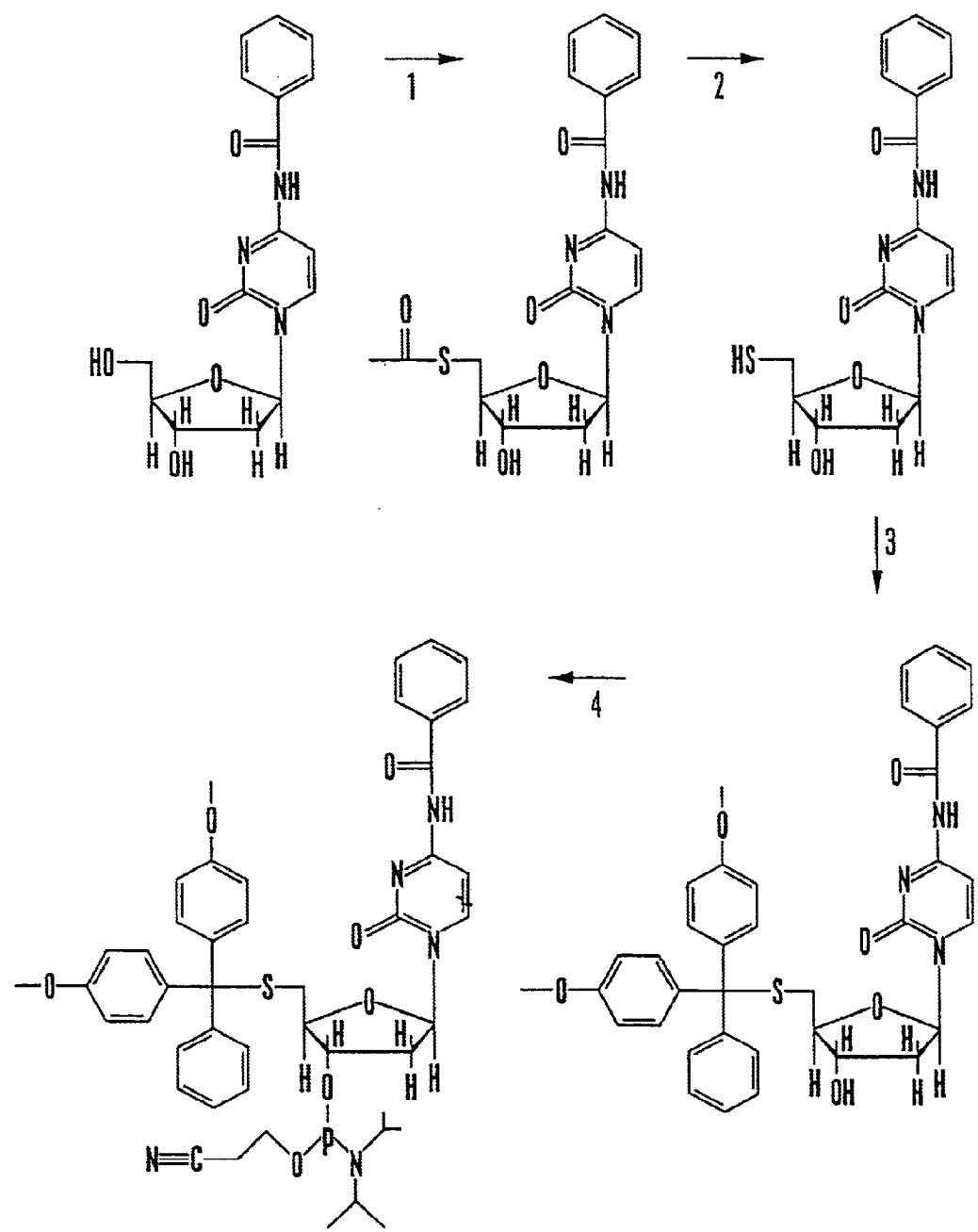
FIG. 7A is a schematic representation of the chemical synthesis of 5'-phosphorothiolate nucleic acid 5'-S- dimethoxytrityl-3'-O-cyanoethyl-NN-diisopropyl-phosphoramidite-2'-deoxy-N-benzoyl-cytosine.

FIG. 7A shows a schematic representation of the chemical synthesis of the 5'-phosphorothiolate nucleic acid 5'-S-dimethoxytrityl-3'-O-cyanoethyl-NN-diisopropyl-phosphoramidite-2'-deoxy-N-benzoyl-cytosine. Preparation of the compound was performed as follows:

N-benzoyl-2'-deoxy cytosine (3.13 mmoles) was dissolved in anhydrous tetrahydrofuran (THF) at 70° C. and allowed to cool to 25° C. Triphenyl phosphine (3.75 mmoles), diethyl azodicarboxylate (3.29 mmoles), and thiolacetic acid (3.44 mmoles) were added sequentially. The reaction was stirred at 25° C. for 6 hours and quenched by adding 5 ml anhydrous methanol, and dried in vacuo. The residue was resuspended in ethyl acetate, and extracted with 3 volumes 5% sodium bicarbonate. Organic layer was dried in vacuo and the product purified silica gel chromatography (5% methanol in dichloromethane).

5'-thio-acetate derivative was dissolved in 20 ml anhydrous methanol and 10 ml anhydrous pyridine was added. 6 ml of 2N NaOH in methanol was added, and the reaction was then stirred at room temp for 5 minutes. The reaction was cooled to 0° C., and 975 ul of concentrated HCL was added followed by 100 ml of 5% phosphate buffer pH 7.0. The aqueous phase was extracted 2x with 100 ml ethyl acetate. The organic phase was dried in vacuo and the 5'-deoxy-5'-sulfhydryl nucleoside was purified by silica gel chromatography (10% methanol in dichloromethane). All solvents were extensively degassed and purged with argon.

5'-deoxy-5'-sulfhydryl-2'-deoxy-N-benzoyl-cytosine (2 mmoles) was dissolved in anhydrous pyridine and dimethoxy-trityl chloride (2.2 mmoles) was added under argon. The reaction was stirred at room temperature for 1 hour, and then quenched by adding 100 ul of beta-mercaptoethanol. The reaction was dried in vacuo, resuspended in dichloromethane, and purified by silica gel chromatography (5% methanol, 0.5% beta-mercaptoethanol in dichloromethane).

5'-S-dimethoxytrityl-2'-deoxy-N-benzoyl-cytosine (1 mmole) was dissolved in anhydrous acetonitrile and NN-diisopropyl-ethylamine (1.2 mmoles) and 2-cyanoethyl diisopropyl-chlorophosphoramidite (1.1 mmoles) were added sequentially at room temp. The reaction was stirred for 60 minutes and quenched with 100 ul of anhydrous methanol. The mixture was dried in vacuo and the product purified by silica gel chromatography (45% ethyl acetate, 25% dichloromethane, 10% triethylamine).

Figure 7B:
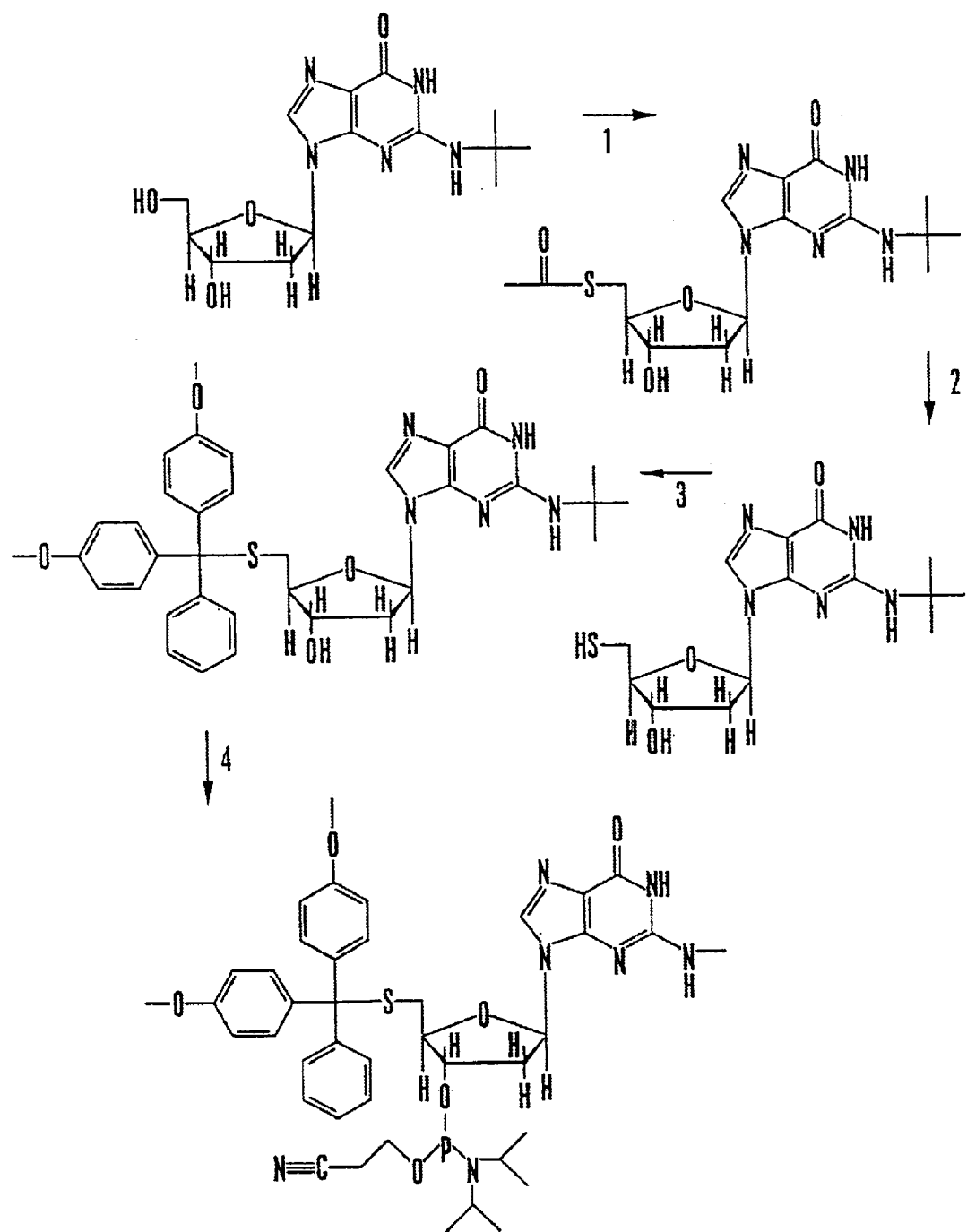
FIG. 7B is a schematic representation of the chemical synthesis of 5'-S-dimethoxytrityl-3'-O-cyanoethyl-NN-diisopropyl-phosphoramidite-2'-deoxy-N-isobutyryl guanosine.

FIG. 7B shows a schematic representation of the chemical synthesis of 5'-S-dimethoxytrityl-3'-O-cyanoethyl-NN-diisopropyl-phosphoramidite-2'-deoxy-N-isobutyryl guanosine. The compound was prepared as follows:

N-benzoyl-2'-deoxy cytosine (3.13 mmoles) was dissolved in anhydrous dimethyl formamide (DMF). Triphenyl phosphine (3.75 mmoles), diethyl azodicarboxylate (3.29 mmoles), and thiolacetic acid (3.44 mmoles) were added sequentially. The reaction was stirred at 25° C. for 6 hours and quenched by adding 5 ml anhydrous methanol. Two volumes of water were added and mixture cooled to −20° C. The precipitate was collected by filtration, resuspended in ethyl acetate, and extracted with 3 volumes 5% sodium bicarbonate. The resulting organic layer was dried in vacuo and the product purified by silica gel chromatography (10% methanol in dichloromethane).

5'-thio-acetate derivative was dissolved in 20 ml anhydrous methanol and 10 ml anhydrous pyridine was added. 6 ml of 2N NaOH in methanol was added, and the reaction was then stirred at room temp for 5 minutes. The reaction was cooled to 0° C., and 975 ul of concentrated HCL was added followed by 100 ml of 5% phosphate buffer pH 7.0. The aqueous phase was extracted 2x with 100 ml ethyl acetate. The organic phase was dried in vacuo and the 5'-deoxy-5'-sulfhydryl nucleoside was purified by silica gel chromatography (10% methanol in dichloromethane).

Note: all solvents were extensively degassed and purged with argon.

5'-deoxy-5'-sulfhydryl-2'-deoxy-N-isobutyryl guanosine (2 mmoles) was dissolved in anhydrous pyridine and dimethoxy-trityl chloride (2.2 mmoles) was added under argon. The reaction was stirred at room temperature for 1 hour, and then quenched by adding 100 ul of beta-mercaptoethanol. The reaction was dried in vacuo, resuspended in dichloromethane, and purified by silica gel chromatography (5% methanol, 0.5% beta-mercaptoethanol in dichloromethane).

5'-S-dimethoxytrityl-2'-deoxy-N-isobutyryl guanosine (1 mmole) was dissolved in anhydrous acetonitrile and NN-diisopropyl-ethylamine (1.2 mmoles) and 2-cyanoethyl diisopropyl-chlorophosphoramidite (1.1 mmoles) were added sequentially at room temp. The reaction was stirred for 60 minutes and quenched with 100 ul of anhydrous methanol. The mixture was dried in vacuo and the product purified by silica gel chromatography (45% ethyl acetate, 25% dichloromethane, 10% triethylamine).

The phosphoramidites were added to the growing oligonucleotide chain using an ABI 392 DNA synthesizer using standard reagents with the exception of the 5'-S-DMT deprotection step.

The 5'-O-DMT protecting group was removed using 2-3% trichloroacetic acid in dichloromethane (standard protocol). Heavy metals (e.g. silver nitrate or mercuric chloride) have been used to remove the 5'-S-Trityl or 5'-S-DMT group. It was observed that 7.5% trichloroacetic acid, 1% betamer-captoethanol in dichloromethane, followed by extensive washing with degassed (argon purged) anhydrous acetonitrile was efficient for removing the DMT and exposing the 5'-sulfhydryl for coupling. To form the phosphorothiolate linkage, the coupling time was increased to 300 minutes.

EXAMPLE VII

Synthesis of a Polynucleotide-3'-Phosphorothiolate

This Example shows an exemplary protocol for one step synthesis of a polynucleotide-3' phosphorothiolate.

Figure 8:
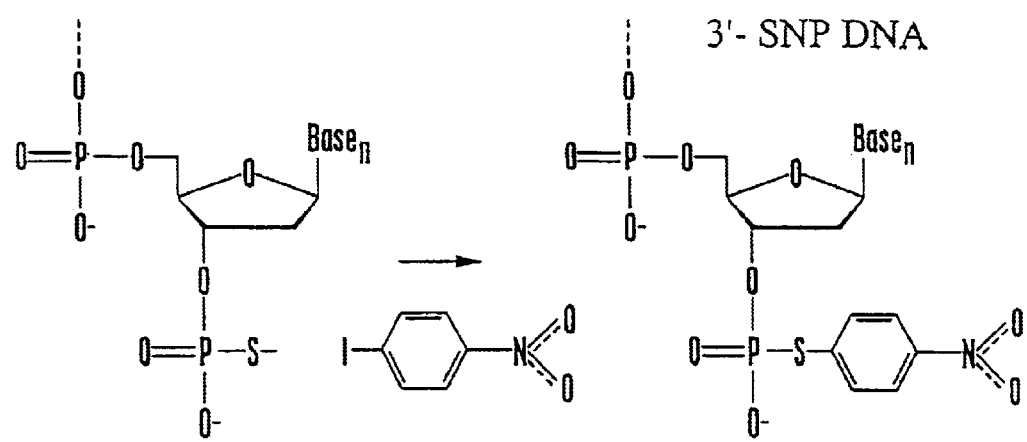
FIG. 8 is a schematic representation of the one-step synthesis of a polynucleotide-3' phosphorothiolate.

A polynucleotide-3' phosphorothiolate (3'-SNP) was prepared by incubating 3'-monophosphorothiolate polynucleotide with 4'-iodo-nitrophenyl, as shown in FIG. 8. Oligonucleotides containing a 3'-monophosphorothioate were synthesized using 3'-phosphate CPG (Glen Research, Sterling, Va.) and standard DNA phosphoramidites on an ABI 392 DNA synthesizer. The first coupling step was sulfurized, rather than oxidized, so that polynucleotide containing a 3'-monophosphorothioate, rather than a 3'-phosphate, was produced following deprotection. The purified oligonucleotide was incubated with saturating concentrations of 4'-iodo-nitrophenyl (Aldrich, St. Louis, Mo.) in 50% water, 50% acetonitrile, 50 mM MES, pH 6.0, 1 mM $MgCl_2$, overnight at 37° C. with vigorous shaking. In FIG. 8, the starting material 3'-monophosphorothioate polynucleotide is shown on the left, the product 3'-SNP polynucleotide is shown on the right, while the activator, 4-iodo-nitrophenyl, is pictured in the center.

After incubation, two volumes of water were added to the reaction mixture, and the mixture was clarified by centrifugation. The solution was then extracted three times with ethyl acetate, and the polynucleotide-3' phosphorothioate is precipitated from the aqueous phase by adding one tenth volume of 3M sodium acetate and three volumes of absolute ethanol.

Thus, a polynucleotide-3' phosphorothiolate was prepared by reacting a polynucleotide-3' phosphorothiolate precursor, 3'-monophosphorothioate polynucleotide, with an activator, 4-iodo-nitrophenyl, using commercially available reagents.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. A method of non-enzymatic ligation of a nucleic acid, comprising contacting a first polynucleotide comprising a polynucleotide-3' phosphorothiolate with an acceptor polynucleotide under conditions that allow nucleophilic attack by a 5'—OH group of the acceptor polynucleotide on the polynucleotide-3' phosphorothiolate to form a phosphodiester bond between said first polynucleotide, and said acceptor polynucleotide, wherein a phosphodiester bond is formed between said first polynucleotide and said acceptor polynucleotide, whereby a ligated nucleic acid product is generated.

2. The method of claim 1, wherein said first polynucleotide comprising a polynucleotide-3' phosphorothiolate comprises a moiety having the formula:

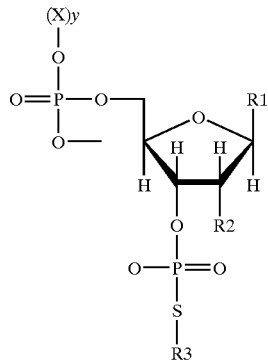

wherein,
X is a nucleotide;
y is a positive integer;
R1 is a nucleotide base;
R2 is a hydrogen atom or hydroxyl; and
R3 is nitrophenyl.

3. The method of claim 1, wherein said first polynucleotide comprising a polynucleotide-3' phosphorothiolate further comprises a duplex polynucleotide.

4. The method of claim 1, wherein said acceptor polynucleotide further comprises a duplex polynucleotide.

5. A method of replicating a ligated nucleic acid product, comprising:

(a) contacting a first polynucleotide comprising a polynucleotide-3' phosphorothiolate with an acceptor polynucleotide under conditions that allow nucleophilic attach by a 5' —OH group of the acceptor polynucleotide on the polynucleotide-3' phosphorothiolate to form a phosphodiester bond between said first polynucleotide and said acceptor polynucleotide, wherein a phosphodiester bond is formed between said first polynucleotide and said acceptor polynucleotide to generate a ligated nucleic acid product, wherein one of said first polynucleotide or said acceptor polynucleotide comprises a vector, and (b) transducing into a host cell said ligated nucleic acid product, wherein said polynucleotide product is replicated in said host cell.

6. A method of non-enzymatic ligation of a nucleic acid, comprising:

(a) contacting a polynucleotide-3' phosphorothiolate precursor and an activator under conditions sufficient to react said polynucleotide-3' phosphorothiolate precursor and said activator, wherein said polynucleotide-3' phosphorothiolate precursor reacts with said activator to produce an intermediate polynucleotide comprising a polynucleotide-3' phosphorothiolate, and (b) contacting said intermediate polynucleotide with an acceptor polynucleotide under conditions that allow nucleophilic attack by a 5'—OH group of the acceptor polynucleotide on said polynucleotide-3' phosphorothiolate to form a phosphodiester bond between said intermediate polynucleotide and said acceptor polynucleotide, wherein a phosphodiester bond is formed between said intermediate polynucleotide and said acceptor polynucleotide, whereby a ligated nucleic acid product is generated.

7. The method of claim 6, wherein said activator is iodonitrobenzene.

8. A method of ligating a vector and an insert comprising, contacting an insert comprising a polynucleotide-3' phosphorothiolate with an acceptor vector under conditions that allow nucleophilic attack by a 5'—OH group of the acceptor vector on the polynucleotide-3' phosphorothiolate of the insert to form a phosphodiester bond between said insert and said acceptor vector, wherein a phosphodiester bond is formed between said insert and said acceptor vector, whereby a ligated product vector comprising said insert is generated.

9. The method of claim 8, further comprising transforming said vector comprising said insert into a host cell.

10. The method of claim 8, wherein said polynucleotide-3' phosphorothiolate comprises a moiety having the formula:

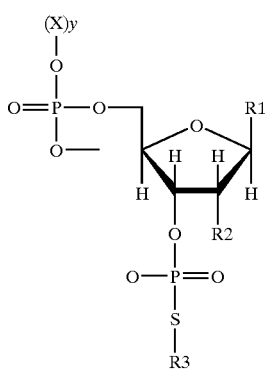

wherein,
X is a nucleotide;
y is a positive integer;
R1 is a nucleotide base;
R2 is a hydrogen atom or hydroxyl; and
R3 is nitrophenyl.

11. A method of ligating a vector and an insert comprising:
   (a) contacting a polynucleotide-3' phosphorothiolate precursor and iodonitrobenzene under conditions sufficient to react said polynucleotide-3' phosphorothiolate precursor and said iodonitrobenzene, wherein said polynucleotide-3' phosphorothiolate precursor reacts with said iodonitrobenzene to produce a polynucleotide-3' phosphorothiolate, and
   (b) contacting an insert comprising said polynucleotide-3' phosphorothiolate with an acceptor vector under conditions that allow formation of a phosphodiester bond between said insert and said acceptor vector, wherein a phosphodiester bond is formed between said insert and said acceptor vector, whereby a ligated product vector comprising said insert is generated.

12. A method of ligating a vector and an acceptor polynucleotide comprising, contacting a vector comprising a polynucleotide-3' phosphorothiolate with an acceptor polynucleotide, under conditions that allow nucleophilic attack by a 5'—OH group of the acceptor polynucleotide on the 3'-phosphorothiolate of the vector to form a phosphodiester bond between said vector and said acceptor polynucleotide, wherein a phosphodiester bond is formed between said vector and said acceptor polynucleotide, whereby a ligated product vector comprising said acceptor polynucleotide is generated.

13. The method of claim 1, further comprising transforming said vector comprising said acceptor polynucleotide into a hot cell.

14. The method of claim 12, wherein said polynucleotide-3' phosphorothiolate comprises a moiety having the formula:

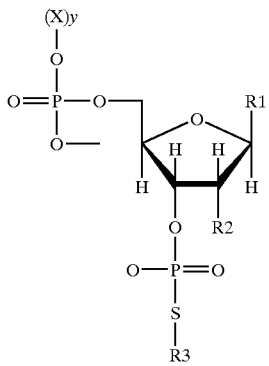

wherein,
X is a nucleotide;
y is a positive integer;
R1 is a nucleotide base;
R2 is a hydrogen atom or hydroxyl; and
R3 is nitrophenyl.

15. The method of claim 12, wherein said vector further comprises a 3' phosphorothiolate moiety at one or more terminal ends of said vector.

16. A method of ligating a vector and acceptor polynucleotide comprising:
   (a) contacting a vector comprising a polynucleotide-3' phosphorothiolate precursor with an activator under conditions sufficient to react said polynucleotide-3' phosphorothiolate precursor and said activator to produce a polynucleotide-3' phosphorothiolate, wherein said polynucleotide-3' phosphorothiolate precursor reacts with said activator to produce a polynucleotide-3' phosphorothiolate, and
   (b) contacting said vector comprising said polynucleotide-3' phosphorothiolate with an acceptor polynucleotide, under conditions that allow nucleophilic attack by a 5'—OH group of the acceptor polynucleotide on the polynucleotide-3' phosphorothiolate to form a phosphodiester bond between said vector and said acceptor polynucleotide, wherein a phosphodiester bond is formed between said vector and said acceptor polynucleotide, whereby a ligated product vector comprising said acceptor polynucleotide is generated.

* * * * *

```
                              SEQUENCE LISTING

<160> NUMBER OF SEQ ID NOS: 19

<210> SEQ ID NO 1
<211> LENGTH: 3739
<212> TYPE: DNA
<213> ORGANISM: Homo sapiens
<220> FEATURE:
<221> NAME/KEY: CDS
<222> LOCATION: (247)...(2541)

<400> SEQUENCE: 1
caaatgcgaa cttaggctgt tacacaactg ctggggtctg ttctcgccgc ccgcccggca      60
gtcaggcagc gtcgccgccg tggtagcagc ctcagccgtt tctggagtct cgggcccaca     120
gtcaccgccg cttacctgcg cctcctcgag cctccggagt ccccgtccgc ccgcacaggc     180
cggttcgccg tctgcgtctc ccccacgccg cctcgcctgc cgccgcgctc gtccctccgg     240 gccgac atg agt ggg gac cac ctc cac aac gat tcc cag atc gaa gcg        288
       Met Ser Gly Asp His Leu His Asn Asp Ser Gln Ile Glu Ala
       1               5                   10 gat ttc cga ttg aat gat tct cat aaa cac aaa gat aaa cac aaa gat       336
Asp Phe Arg Leu Asn Asp Ser His Lys His Lys Asp Lys His Lys Asp
15                  20                  25                  30 cga gaa cac cgg cac aaa gaa cac aag aag gag aag gac cgg gaa aag       384
Arg Glu His Arg His Lys Glu His Lys Lys Glu Lys Asp Arg Glu Lys
                35                  40                  45 tcc aag cat agc aac agt gaa cat aaa gat tct gaa aag aaa cac aaa       432
Ser Lys His Ser Asn Ser Glu His Lys Asp Ser Glu Lys Lys His Lys
            50                  55                  60 gag aag gag aag acc aaa cac aaa gat gga agc tca gaa aag cat aaa       480
Glu Lys Glu Lys Thr Lys His Lys Asp Gly Ser Ser Glu Lys His Lys
        65                  70                  75 gac aaa cat aaa gac aga gac aag gaa aaa cga aaa gag gaa aag gtt       528
Asp Lys His Lys Asp Arg Asp Lys Glu Lys Arg Lys Glu Glu Lys Val
    80                  85                  90 cga gcc tct ggg gat gca aaa ata aag aag gag aag gaa aat ggc ttc       576
Arg Ala Ser Gly Asp Ala Lys Ile Lys Lys Glu Lys Glu Asn Gly Phe
95                  100                 105                 110 tct agt cca cca caa att aaa gat gaa cct gaa gat gat ggc tat ttt       624
Ser Ser Pro Pro Gln Ile Lys Asp Glu Pro Glu Asp Asp Gly Tyr Phe
                115                 120                 125 gtt cct cct aaa gag gat ata aag cca tta aag aga cct cga gat gag       672
Val Pro Pro Lys Glu Asp Ile Lys Pro Leu Lys Arg Pro Arg Asp Glu
            130                 135                 140 gat gat gct gat tat aaa cct aag aaa att aaa aca gaa gat acc aag       720
Asp Asp Ala Asp Tyr Lys Pro Lys Lys Ile Lys Thr Glu Asp Thr Lys
        145                 150                 155 aag gag aag aaa aga aaa cta gaa gaa gaa gag gat ggt aaa ttg aaa       768
```

```
                Lys Glu Lys Lys Arg Lys Leu Glu Glu Glu Asp Gly Lys Leu Lys
                160                 165                 170 aaa ccc aag aat aaa gat aaa gat aaa aaa gtt cct gag cca gat aac           816
Lys Pro Lys Asn Lys Asp Lys Asp Lys Lys Val Pro Glu Pro Asp Asn
175                 180                 185                 190 aag aaa aag aag ccg aag aaa gaa gag gaa cag aag tgg aaa tgg tgg           864
Lys Lys Lys Lys Pro Lys Lys Glu Glu Glu Gln Lys Trp Lys Trp Trp
                195                 200                 205 gaa gaa gag cgc tat cct gaa ggc atc aag tgg aaa ttc cta gaa cat           912
Glu Glu Glu Arg Tyr Pro Glu Gly Ile Lys Trp Lys Phe Leu Glu His
                210                 215                 220 aaa ggt cca gta ttt gcc cca cca tat gag cct ctt cca gag aat gtc           960
Lys Gly Pro Val Phe Ala Pro Pro Tyr Glu Pro Leu Pro Glu Asn Val
            225                 230                 235 aag ttt tat tat gat ggt aaa gtc atg aag ctg agc ccc aaa gca gag          1008
Lys Phe Tyr Tyr Asp Gly Lys Val Met Lys Leu Ser Pro Lys Ala Glu
        240                 245                 250 gaa gta gct acg ttc ttt gca aaa atg ctc gac cat gaa tat act acc          1056
Glu Val Ala Thr Phe Phe Ala Lys Met Leu Asp His Glu Tyr Thr Thr
255                 260                 265                 270 aag gaa ata ttt agg aaa aat ttc ttt aaa gac tgg aga aag gaa atg          1104
Lys Glu Ile Phe Arg Lys Asn Phe Phe Lys Asp Trp Arg Lys Glu Met
                275                 280                 285 act aat gaa gag aag aat att atc acc aac cta agc aaa tgt gat ttt          1152
Thr Asn Glu Glu Lys Asn Ile Ile Thr Asn Leu Ser Lys Cys Asp Phe
                290                 295                 300 acc cag atg agc cag tat ttc aaa gcc cag acg gaa gct cgg aaa cag          1200
Thr Gln Met Ser Gln Tyr Phe Lys Ala Gln Thr Glu Ala Arg Lys Gln
            305                 310                 315 atg agc aag gaa gag aaa ctg aaa atc aaa gag gag aat gaa aaa tta          1248
Met Ser Lys Glu Glu Lys Leu Lys Ile Lys Glu Glu Asn Glu Lys Leu
        320                 325                 330 ctg aaa gaa tat gga ttc tgt att atg gat aac cac aaa gag agg att          1296
Leu Lys Glu Tyr Gly Phe Cys Ile Met Asp Asn His Lys Glu Arg Ile
335                 340                 345                 350 gct aac ttc aag ata gag cct cct gga ctt ttc cgt ggc cgc ggc aac          1344
Ala Asn Phe Lys Ile Glu Pro Pro Gly Leu Phe Arg Gly Arg Gly Asn
                355                 360                 365 cac ccc aag atg ggc atg ctg aag aga cga atc atg ccc gag gat ata          1392
His Pro Lys Met Gly Met Leu Lys Arg Arg Ile Met Pro Glu Asp Ile
            370                 375                 380 atc atc aac tgt agc aaa gat gcc aag gtt cct tct cct cct cca gga          1440
Ile Ile Asn Cys Ser Lys Asp Ala Lys Val Pro Ser Pro Pro Pro Gly
        385                 390                 395 cat aag tgg aaa gaa gtc cgg cat gat aac aag gtt act tgg ctg gtt          1488
His Lys Trp Lys Glu Val Arg His Asp Asn Lys Val Thr Trp Leu Val
400                 405                 410 tcc tgg aca gag aac atc caa ggt tcc att aaa tac atc atg ctt aac          1536
Ser Trp Thr Glu Asn Ile Gln Gly Ser Ile Lys Tyr Ile Met Leu Asn
415                 420                 425                 430 cct agt tca cga atc aag ggt gag aag gac tgg cag aaa tac gag act          1584
Pro Ser Ser Arg Ile Lys Gly Glu Lys Asp Trp Gln Lys Tyr Glu Thr
                435                 440                 445 gct cgg cgg ctg aaa aaa tgt gtg gac aag atc cgg aac cag tat cga          1632
Ala Arg Arg Leu Lys Lys Cys Val Asp Lys Ile Arg Asn Gln Tyr Arg
            450                 455                 460 gaa gac tgg aag tcc aaa gag atg aaa gtc cgg cag aga gct gta gcc          1680
Glu Asp Trp Lys Ser Lys Glu Met Lys Val Arg Gln Arg Ala Val Ala
        465                 470                 475
```

```
                                                      -continued
ctg tac ttc atc gac aag ctt gct ctg aga gca ggc aat gaa aag gag      1728
Leu Tyr Phe Ile Asp Lys Leu Ala Leu Arg Ala Gly Asn Glu Lys Glu
    480                 485                 490 gaa gga gaa aca gcg gac act gtg ggc tgc tgc tca ctt cgt gtg gag      1776
Glu Gly Glu Thr Ala Asp Thr Val Gly Cys Cys Ser Leu Arg Val Glu
495                 500                 505                 510 cac atc aat cta cac cca gag ttg gat ggt cag gaa tat gtg gta gag      1824
His Ile Asn Leu His Pro Glu Leu Asp Gly Gln Glu Tyr Val Val Glu
                515                 520                 525 ttt gac ttc ctc ggg aag gac tcc atc aga tac tat aac aag gtc cct      1872
Phe Asp Phe Leu Gly Lys Asp Ser Ile Arg Tyr Tyr Asn Lys Val Pro
            530                 535                 540 gtt gag aaa cga gtt ttt aag aac cta caa cta ttt atg gag aac aag      1920
Val Glu Lys Arg Val Phe Lys Asn Leu Gln Leu Phe Met Glu Asn Lys
        545                 550                 555 cag ccc gag gat gat ctt ttt gat aga ctc aat act ggt att ctg aat      1968
Gln Pro Glu Asp Asp Leu Phe Asp Arg Leu Asn Thr Gly Ile Leu Asn
    560                 565                 570 aag cat ctt cag gat ctc atg gag ggc ttg aca gcc aag gta ttc cgt      2016
Lys His Leu Gln Asp Leu Met Glu Gly Leu Thr Ala Lys Val Phe Arg
575                 580                 585                 590 aca tac aat gcc tcc atc acg cta cag cag cag cta aaa gaa ctg aca      2064
Thr Tyr Asn Ala Ser Ile Thr Leu Gln Gln Gln Leu Lys Glu Leu Thr
                595                 600                 605 gcc ccg gat gag aac atc cca gcg aag atc ctt tct tat aac cgt gcc      2112
Ala Pro Asp Glu Asn Ile Pro Ala Lys Ile Leu Ser Tyr Asn Arg Ala
            610                 615                 620 aat cga gct gtt gca att ctt tgt aac cat cag agg gca cca cca aaa      2160
Asn Arg Ala Val Ala Ile Leu Cys Asn His Gln Arg Ala Pro Pro Lys
        625                 630                 635 act ttt gag aag tct atg atg aac ttg caa act aag att gat gcc aag      2208
Thr Phe Glu Lys Ser Met Met Asn Leu Gln Thr Lys Ile Asp Ala Lys
    640                 645                 650 aag gaa cag cta gca gat gcc cgg aga gac ctg aaa agt gct aag gct      2256
Lys Glu Gln Leu Ala Asp Ala Arg Arg Asp Leu Lys Ser Ala Lys Ala
655                 660                 665                 670 gat gcc aag gtc atg aag gat gca aag acg aag aag gta gta gag tca      2304
Asp Ala Lys Val Met Lys Asp Ala Lys Thr Lys Lys Val Val Glu Ser
                675                 680                 685 aag aag aag gct gtt cag aga ctg gag gaa cag ttg atg aag ctg gaa      2352
Lys Lys Lys Ala Val Gln Arg Leu Glu Glu Gln Leu Met Lys Leu Glu
            690                 695                 700 gtt caa gcc aca gac cga gag gaa aat aaa cag att gcc ctg gga acc      2400
Val Gln Ala Thr Asp Arg Glu Glu Asn Lys Gln Ile Ala Leu Gly Thr
        705                 710                 715 tcc aaa ctc aat tat ctg gac cct agg atc aca gtg gct tgg tgc aag      2448
Ser Lys Leu Asn Tyr Leu Asp Pro Arg Ile Thr Val Ala Trp Cys Lys
    720                 725                 730 aag tgg ggt gtc cca att gag aag att tac aac aaa acc cag cgg gag      2496
Lys Trp Gly Val Pro Ile Glu Lys Ile Tyr Asn Lys Thr Gln Arg Glu
735                 740                 745                 750 aag ttt gcc tgg gcc att gac atg gct gat gaa gac tat gag ttt          2541
Lys Phe Ala Trp Ala Ile Asp Met Ala Asp Glu Asp Tyr Glu Phe
                755                 760                 765 tagccagtct caagaggcag agttctgtga agaggaacag tgtggtttgg gaaagatgga    2601
taaactgagc ctcacttgcc ctcgtgcctg ggggagagag gcagcaagtc ttaacaaacc    2661
aacatctttg cgaaaagata aacctggaga tattataagg gagagctgag ccagttgtcc    2721
tatggacaac ttatttaaaa atatttcaga tatcaaaatt ctagctgtat gatttgtttt    2781
```

```
gaattttgtt ttattttca agagggcaag tggatgggaa tttgtcagcg ttctaccagg    2841
caaattcact gtttcactga aatgtttgga ttctcttagc tactgtatgc aaagtccgat    2901
tatattggtg cgttttaca gttagggttt tgcaataact tctatatttt aatagaaata    2961
aattcctaaa ctcccttccc tctctcccat tcaggaatt taaaattaag tagaacaaaa    3021
aacccagcgc acctgttaga gtcgtcactc tctattgtca tggggatcaa ttttcattaa    3081
acttgaagca gtcgtggctt tggcagtgtt ttggttcaga cacctgttca cagaaaaagc    3141
atgatgggaa aatatttcct gacttgagtg ttccttttta aatgtgaatt tttatttctt    3201
tttaattatt ttaaaatatt taaaccttt tcttgatctt aaagatcgtg tagattgggg    3261
ttggggaggg atgaagggcg agtgaatcta aggataatga aataatcagt gactgaaacc    3321
attttcccat catcctttgt tctgagcatt cgctgtaccc tttaagatat ccatcttttt    3381 cttttttaacc ctaatctttc acttgaaaga ttttattgta taaaaagttt cacaggtcaa    3441
taaacttaga ggaaaatgag tatttggtcc aaaaaaagga aaaataatca agattttagg    3501
gcttttattt tttcttttgt aattgtgtaa aaaatggaaa aaaacataaa aagcagaatt    3561
ttaatgtgaa gacatttttt gctataatca ttagttttag aggcattgtt agtttagtgt    3621
gtgtgcagag tccatttccc acatctttcc tcaagtatct tctattttta tcatgaattc    3681
ccttttaatc aactgtaggt tatttaaaat aaattcctac aacttaatgg aaacttaa     3739
```

<210> SEQ ID NO 2
<211> LENGTH: 765
<212> TYPE: PRT
<213> ORGANISM: Homo sapiens

<400> SEQUENCE: 2

```
Met Ser Gly Asp His Leu His Asn Asp Ser Gln Ile Glu Ala Asp Phe
 1               5                  10                  15

Arg Leu Asn Asp Ser His Lys His Asp Lys His Lys Asp Arg Glu
                20                  25                  30

His Arg His Lys Glu His Lys Lys Glu Lys Asp Arg Glu Lys Ser Lys
             35                  40                  45

His Ser Asn Ser Glu His Lys Asp Ser Glu Lys Lys His Lys Glu Lys
         50                  55                  60

Glu Lys Thr Lys His Lys Asp Gly Ser Ser Glu Lys His Lys Asp Lys
 65                  70                  75                  80

His Lys Asp Arg Asp Lys Glu Lys Arg Lys Glu Lys Val Arg Ala
                 85                  90                  95

Ser Gly Asp Ala Lys Ile Lys Lys Glu Lys Glu Asn Gly Phe Ser Ser
            100                 105                 110

Pro Pro Gln Ile Lys Asp Glu Pro Glu Asp Asp Gly Tyr Phe Val Pro
        115                 120                 125

Pro Lys Glu Asp Ile Lys Pro Leu Lys Arg Pro Arg Asp Glu Asp Asp
    130                 135                 140

Ala Asp Tyr Lys Pro Lys Lys Ile Lys Thr Glu Asp Thr Lys Lys Glu
145                 150                 155                 160

Lys Lys Arg Lys Leu Glu Glu Glu Glu Asp Gly Lys Leu Lys Lys Pro
                165                 170                 175

Lys Asn Lys Asp Lys Asp Lys Val Pro Glu Pro Asp Asn Lys Lys
            180                 185                 190

Lys Lys Pro Lys Lys Glu Glu Glu Gln Lys Trp Lys Trp Trp Glu Glu
        195                 200                 205
```

-continued

```
Glu Arg Tyr Pro Glu Gly Ile Lys Trp Lys Phe Leu Glu His Lys Gly
210                 215                 220

Pro Val Phe Ala Pro Pro Tyr Glu Pro Leu Pro Glu Asn Val Lys Phe
225                 230                 235                 240

Tyr Tyr Asp Gly Lys Val Met Lys Leu Ser Pro Lys Ala Glu Glu Val
                245                 250                 255

Ala Thr Phe Phe Ala Lys Met Leu Asp His Glu Tyr Thr Thr Lys Glu
                260                 265                 270

Ile Phe Arg Lys Asn Phe Phe Lys Asp Trp Arg Lys Glu Met Thr Asn
            275                 280                 285

Glu Glu Lys Asn Ile Ile Thr Asn Leu Ser Lys Cys Asp Phe Thr Gln
290                 295                 300

Met Ser Gln Tyr Phe Lys Ala Gln Thr Glu Ala Arg Lys Gln Met Ser
305                 310                 315                 320

Lys Glu Glu Lys Leu Lys Ile Lys Glu Glu Asn Glu Lys Leu Leu Lys
                325                 330                 335

Glu Tyr Gly Phe Cys Ile Met Asp Asn His Lys Glu Arg Ile Ala Asn
                340                 345                 350

Phe Lys Ile Glu Pro Pro Gly Leu Phe Arg Gly Arg Gly Asn His Pro
            355                 360                 365

Lys Met Gly Met Leu Lys Arg Arg Ile Met Pro Glu Asp Ile Ile Ile
370                 375                 380

Asn Cys Ser Lys Asp Ala Lys Val Pro Ser Pro Pro Gly His Lys
385                 390                 395                 400

Trp Lys Glu Val Arg His Asp Asn Lys Val Thr Trp Leu Val Ser Trp
                405                 410                 415

Thr Glu Asn Ile Gln Gly Ser Ile Lys Tyr Ile Met Leu Asn Pro Ser
                420                 425                 430

Ser Arg Ile Lys Gly Glu Lys Asp Trp Gln Lys Tyr Glu Thr Ala Arg
            435                 440                 445

Arg Leu Lys Lys Cys Val Asp Lys Ile Arg Asn Gln Tyr Arg Glu Asp
450                 455                 460

Trp Lys Ser Lys Glu Met Lys Val Arg Gln Arg Ala Val Ala Leu Tyr
465                 470                 475                 480

Phe Ile Asp Lys Leu Ala Leu Arg Ala Gly Asn Glu Lys Glu Glu Gly
                485                 490                 495

Glu Thr Ala Asp Thr Val Gly Cys Cys Ser Leu Arg Val Glu His Ile
                500                 505                 510

Asn Leu His Pro Glu Leu Asp Gly Gln Glu Tyr Val Val Glu Phe Asp
            515                 520                 525

Phe Leu Gly Lys Asp Ser Ile Arg Tyr Tyr Asn Lys Val Pro Val Glu
530                 535                 540

Lys Arg Val Phe Lys Asn Leu Gln Leu Phe Met Glu Asn Lys Gln Pro
545                 550                 555                 560

Glu Asp Asp Leu Phe Asp Arg Leu Asn Thr Gly Ile Leu Asn Lys His
                565                 570                 575

Leu Gln Asp Leu Met Glu Gly Leu Thr Ala Lys Val Phe Arg Thr Tyr
                580                 585                 590

Asn Ala Ser Ile Thr Leu Gln Gln Leu Lys Glu Leu Thr Ala Pro
            595                 600                 605

Asp Glu Asn Ile Pro Ala Lys Ile Leu Ser Tyr Asn Arg Ala Asn Arg
610                 615                 620
```

-continued

```
Ala Val Ala Ile Leu Cys Asn His Gln Arg Ala Pro Pro Lys Thr Phe
625                 630                 635                 640

Glu Lys Ser Met Met Asn Leu Gln Thr Lys Ile Asp Ala Lys Lys Glu
            645                 650                 655

Gln Leu Ala Asp Ala Arg Arg Asp Leu Lys Ser Ala Lys Ala Asp Ala
        660                 665                 670

Lys Val Met Lys Asp Ala Lys Thr Lys Lys Val Glu Ser Lys Lys
    675                 680                 685

Lys Ala Val Gln Arg Leu Glu Glu Gln Leu Met Lys Leu Glu Val Gln
690                 695                 700

Ala Thr Asp Arg Glu Glu Asn Lys Gln Ile Ala Leu Gly Thr Ser Lys
705                 710                 715                 720

Leu Asn Tyr Leu Asp Pro Arg Ile Thr Val Ala Trp Cys Lys Lys Trp
                725                 730                 735

Gly Val Pro Ile Glu Lys Ile Tyr Asn Lys Thr Gln Arg Glu Lys Phe
            740                 745                 750

Ala Trp Ala Ile Asp Met Ala Asp Glu Asp Tyr Glu Phe
        755                 760                 765
```

<210> SEQ ID NO 3
<211> LENGTH: 1719
<212> TYPE: DNA
<213> ORGANISM: Artificial Sequence
<220> FEATURE:
<223> OTHER INFORMATION: human fusion
<221> NAME/KEY: CDS
<222> LOCATION: (1)...(1716)

<400> SEQUENCE: 3

```
atg aac aag aaa aag aag ccg aag aaa gaa gag cat cat cat cat cat    48
Met Asn Lys Lys Lys Lys Pro Lys Lys Glu Glu His His His His His
1               5                   10                  15 cac atc gaa ggt cgt atc aag tgg aaa ttc cta gaa cat aaa ggt cca    96
His Ile Glu Gly Arg Ile Lys Trp Lys Phe Leu Glu His Lys Gly Pro
                20                  25                  30 gta ttt gcc cca cca tat gag cct ctt cca gag aat gtc aag ttt tat   144
Val Phe Ala Pro Pro Tyr Glu Pro Leu Pro Glu Asn Val Lys Phe Tyr
            35                  40                  45 tat gat ggt aaa gtc atg aag ctg agc ccc aaa gca gag gaa gta gct   192
Tyr Asp Gly Lys Val Met Lys Leu Ser Pro Lys Ala Glu Glu Val Ala
        50                  55                  60 acg ttc ttt gca aaa atg ctc gac cat gaa tat act acc aag gaa ata   240
Thr Phe Phe Ala Lys Met Leu Asp His Glu Tyr Thr Thr Lys Glu Ile
65                  70                  75                  80 ttt agg aaa aat ttc ttt aaa gac tgg aga aag gaa atg act aat gaa   288
Phe Arg Lys Asn Phe Phe Lys Asp Trp Arg Lys Glu Met Thr Asn Glu
                85                  90                  95 gag aag aat att atc acc aac cta agc aaa tgt gat ttt acc cag atg   336
Glu Lys Asn Ile Ile Thr Asn Leu Ser Lys Cys Asp Phe Thr Gln Met
                100                 105                 110 agc cag tat ttc aaa gcc cag acg gaa gct cgg aaa cag atg agc aag   384
Ser Gln Tyr Phe Lys Ala Gln Thr Glu Ala Arg Lys Gln Met Ser Lys
            115                 120                 125 gaa gag aaa ctg aaa atc aaa gag gag aat gaa aaa tta ctg aaa gaa   432
Glu Glu Lys Leu Lys Ile Lys Glu Glu Asn Glu Lys Leu Leu Lys Glu
        130                 135                 140 tat gga ttc tgt att atg gat aac cac aaa gag agg att gct aac ttc   480
Tyr Gly Phe Cys Ile Met Asp Asn His Lys Glu Arg Ile Ala Asn Phe
145                 150                 155                 160
```

```
                                                        -continued aag ata gag cct cct gga ctt ttc cgt ggc cgc ggc aac cac ccc aag      528
Lys Ile Glu Pro Pro Gly Leu Phe Arg Gly Arg Gly Asn His Pro Lys
            165                 170                 175 atg ggc atg ctg aag aga cga atc atg ccc gag gat ata atc atc aac      576
Met Gly Met Leu Lys Arg Arg Ile Met Pro Glu Asp Ile Ile Ile Asn
        180                 185                 190 tgt agc aaa gat gcc aag gtt cct tct cct cct cca gga cat aag tgg      624
Cys Ser Lys Asp Ala Lys Val Pro Ser Pro Pro Pro Gly His Lys Trp
    195                 200                 205 aaa gaa gtc cgg cat gat aac aag gtt act tgg ctg gtt tcc tgg aca      672
Lys Glu Val Arg His Asp Asn Lys Val Thr Trp Leu Val Ser Trp Thr
210                 215                 220 gag aac atc caa ggt tcc att aaa tac atc atg ctt aac cct agt tca      720
Glu Asn Ile Gln Gly Ser Ile Lys Tyr Ile Met Leu Asn Pro Ser Ser
225                 230                 235                 240 cga atc aag ggt gag aag gac tgg cag aaa tac gag act gct cgg cgg      768
Arg Ile Lys Gly Glu Lys Asp Trp Gln Lys Tyr Glu Thr Ala Arg Arg
            245                 250                 255 ctg aaa aaa tgt gtg gac aag atc cgg aac cag tat cga gaa gac tgg      816
Leu Lys Lys Cys Val Asp Lys Ile Arg Asn Gln Tyr Arg Glu Asp Trp
            260                 265                 270 aag tcc aaa gag atg aaa gtc cgg cag aga gct gta gcc ctg tac ttc      864
Lys Ser Lys Glu Met Lys Val Arg Gln Arg Ala Val Ala Leu Tyr Phe
        275                 280                 285 atc gac aag ctt gct ctg aga gca ggc aat gaa aag gag gaa gga gaa      912
Ile Asp Lys Leu Ala Leu Arg Ala Gly Asn Glu Lys Glu Glu Gly Glu
    290                 295                 300 aca gcg gac act gtg ggc tgc tgc tca ctt cgt gtg gag cac atc aat      960
Thr Ala Asp Thr Val Gly Cys Cys Ser Leu Arg Val Glu His Ile Asn
305                 310                 315                 320 cta cac cca gag ttg gat ggt cag gaa tat gtg gta gag ttt gac ttc     1008
Leu His Pro Glu Leu Asp Gly Gln Glu Tyr Val Val Glu Phe Asp Phe
            325                 330                 335 ctc ggg aag gac tcc atc aga tac tat aac aag gtc cct gtt gag aaa     1056
Leu Gly Lys Asp Ser Ile Arg Tyr Tyr Asn Lys Val Pro Val Glu Lys
            340                 345                 350 cga gtt ttt aag aac cta caa cta ttt atg gag aac aag cag ccc gag     1104
Arg Val Phe Lys Asn Leu Gln Leu Phe Met Glu Asn Lys Gln Pro Glu
        355                 360                 365 gat gat ctt ttt gat aga ctc aat act ggt att ctg aat aag cat ctt     1152
Asp Asp Leu Phe Asp Arg Leu Asn Thr Gly Ile Leu Asn Lys His Leu
    370                 375                 380 cag gat ctc atg gag ggc ttg aca gcc aag gta ttc cgt acg tac aat     1200
Gln Asp Leu Met Glu Gly Leu Thr Ala Lys Val Phe Arg Thr Tyr Asn
385                 390                 395                 400 gcc tcc atc acg cta cag cag cag cta aaa gaa ctg aca gcc ccg gat     1248
Ala Ser Ile Thr Leu Gln Gln Gln Leu Lys Glu Leu Thr Ala Pro Asp
            405                 410                 415 gag aac atc cca gcg aag atc ctt tct tat aac cgt gcc aat cga gct     1296
Glu Asn Ile Pro Ala Lys Ile Leu Ser Tyr Asn Arg Ala Asn Arg Ala
        420                 425                 430 gtt gca att ctt tgt aac cat cag agg gca cca cca aaa act ttt gag     1344
Val Ala Ile Leu Cys Asn His Gln Arg Ala Pro Pro Lys Thr Phe Glu
    435                 440                 445 aag tct atg atg aac ttg caa act aag att gat gcc aag aag gaa cag     1392
Lys Ser Met Met Asn Leu Gln Thr Lys Ile Asp Ala Lys Lys Glu Gln
450                 455                 460 cta gca gat gcc cgg aga gac ctg aaa agt gct aag gct gat gcc aag     1440
Leu Ala Asp Ala Arg Arg Asp Leu Lys Ser Ala Lys Ala Asp Ala Lys
465                 470                 475                 480
```

```
gtc atg aag gat gca aag acg aag aag gta gta gag tca aag aag aag   1488
Val Met Lys Asp Ala Lys Thr Lys Lys Val Val Glu Ser Lys Lys Lys
            485                 490                 495 gct gtt cag aga ctg gag gaa cag ttg atg aag ctg gaa gtt caa gcc   1536
Ala Val Gln Arg Leu Glu Glu Gln Leu Met Lys Leu Glu Val Gln Ala
        500                 505                 510 aca gac cga gag gaa aat aaa cag att gcc ctg gga acc tcc aaa ctc   1584
Thr Asp Arg Glu Glu Asn Lys Gln Ile Ala Leu Gly Thr Ser Lys Leu
    515                 520                 525 aat tat ctg gac cct agg atc aca gtg gct tgg tgc aag aag tgg ggt   1632
Asn Tyr Leu Asp Pro Arg Ile Thr Val Ala Trp Cys Lys Lys Trp Gly
530                 535                 540 gtc cca att gag aag att tac aac aaa acc cag cgg gag aag ttt gcc   1680
Val Pro Ile Glu Lys Ile Tyr Asn Lys Thr Gln Arg Glu Lys Phe Ala
545                 550                 555                 560 tgg gcc att gac atg gct gat gaa gac tat gag ttt tag               1719
Trp Ala Ile Asp Met Ala Asp Glu Asp Tyr Glu Phe
                565                 570

<210> SEQ ID NO 4
<211> LENGTH: 572
<212> TYPE: PRT
<213> ORGANISM: Artificial Sequence
<220> FEATURE:
<223> OTHER INFORMATION: human fusion

<400> SEQUENCE: 4

Met Asn Lys Lys Lys Pro Lys Lys Glu Glu His His His His
1               5                   10                  15

His Ile Glu Gly Arg Ile Lys Trp Lys Phe Leu Glu His Lys Gly Pro
            20                  25                  30

Val Phe Ala Pro Pro Tyr Glu Pro Leu Pro Glu Asn Val Lys Phe Tyr
        35                  40                  45

Tyr Asp Gly Lys Val Met Lys Leu Ser Pro Lys Ala Glu Glu Val Ala
    50                  55                  60

Thr Phe Phe Ala Lys Met Leu Asp His Glu Tyr Thr Thr Lys Glu Ile
65                  70                  75                  80

Phe Arg Lys Asn Phe Phe Lys Asp Trp Arg Lys Glu Met Thr Asn Glu
                85                  90                  95

Glu Lys Asn Ile Ile Thr Asn Leu Ser Lys Cys Asp Phe Thr Gln Met
            100                 105                 110

Ser Gln Tyr Phe Lys Ala Gln Thr Glu Ala Arg Lys Gln Met Ser Lys
        115                 120                 125

Glu Glu Lys Leu Lys Ile Lys Glu Glu Asn Glu Lys Leu Leu Lys Glu
    130                 135                 140

Tyr Gly Phe Cys Ile Met Asp Asn His Lys Glu Arg Ile Ala Asn Phe
145                 150                 155                 160

Lys Ile Glu Pro Pro Gly Leu Phe Arg Gly Arg Gly Asn His Pro Lys
                165                 170                 175

Met Gly Met Leu Lys Arg Arg Ile Met Pro Glu Asp Ile Ile Asn
            180                 185                 190

Cys Ser Lys Asp Ala Lys Val Pro Ser Pro Pro Gly His Lys Trp
        195                 200                 205

Lys Glu Val Arg His Asp Asn Lys Val Thr Trp Leu Val Ser Trp Thr
    210                 215                 220

Glu Asn Ile Gln Gly Ser Ile Lys Tyr Ile Met Leu Asn Pro Ser Ser
225                 230                 235                 240
```

```
Arg Ile Lys Gly Glu Lys Asp Trp Gln Lys Tyr Glu Thr Ala Arg Arg
                245                 250                 255
Leu Lys Lys Cys Val Asp Lys Ile Arg Asn Gln Tyr Arg Glu Asp Trp
            260                 265                 270
Lys Ser Lys Glu Met Lys Val Arg Gln Arg Ala Val Ala Leu Tyr Phe
        275                 280                 285
Ile Asp Lys Leu Ala Leu Arg Ala Gly Asn Glu Lys Glu Gly Glu
    290                 295                 300
Thr Ala Asp Thr Val Gly Cys Cys Ser Leu Arg Val Glu His Ile Asn
305                 310                 315                 320
Leu His Pro Glu Leu Asp Gly Gln Glu Tyr Val Val Glu Phe Asp Phe
                325                 330                 335
Leu Gly Lys Asp Ser Ile Arg Tyr Tyr Asn Lys Val Pro Val Glu Lys
            340                 345                 350
Arg Val Phe Lys Asn Leu Gln Leu Phe Met Glu Asn Lys Gln Pro Glu
        355                 360                 365
Asp Asp Leu Phe Asp Arg Leu Asn Thr Gly Ile Leu Asn Lys His Leu
    370                 375                 380
Gln Asp Leu Met Glu Gly Leu Thr Ala Lys Val Phe Arg Thr Tyr Asn
385                 390                 395                 400
Ala Ser Ile Thr Leu Gln Gln Gln Leu Lys Glu Leu Thr Ala Pro Asp
                405                 410                 415
Glu Asn Ile Pro Ala Lys Ile Leu Ser Tyr Asn Arg Ala Asn Arg Ala
            420                 425                 430
Val Ala Ile Leu Cys Asn His Gln Arg Ala Pro Pro Lys Thr Phe Glu
        435                 440                 445
Lys Ser Met Met Asn Leu Gln Thr Lys Ile Asp Ala Lys Lys Glu Gln
    450                 455                 460
Leu Ala Asp Ala Arg Arg Asp Leu Lys Ser Ala Lys Ala Asp Ala Lys
465                 470                 475                 480
Val Met Lys Asp Ala Lys Thr Lys Lys Val Val Glu Ser Lys Lys Lys
                485                 490                 495
Ala Val Gln Arg Leu Glu Glu Gln Leu Met Lys Leu Glu Val Gln Ala
            500                 505                 510
Thr Asp Arg Glu Glu Asn Lys Gln Ile Ala Leu Gly Thr Ser Lys Leu
        515                 520                 525
Asn Tyr Leu Asp Pro Arg Ile Thr Val Ala Trp Cys Lys Lys Trp Gly
    530                 535                 540
Val Pro Ile Glu Lys Ile Tyr Asn Lys Thr Gln Arg Glu Lys Phe Ala
545                 550                 555                 560
Trp Ala Ile Asp Met Ala Asp Glu Asp Tyr Glu Phe
                565                 570
```

<210> SEQ ID NO 5
<211> LENGTH: 6
<212> TYPE: DNA
<213> ORGANISM: Artificial Sequence
<220> FEATURE:
<223> OTHER INFORMATION: synthetic

<400> SEQUENCE: 5 gycctt                                                              6

<210> SEQ ID NO 6
<211> LENGTH: 22

```
<212> TYPE: DNA
<213> ORGANISM: Artificial Sequence
<220> FEATURE:
<221> NAME/KEY: modified_base
<222> LOCATION: (18)...(19)
<223> OTHER INFORMATION: n=5-bromo-deoxyurindine
<223> OTHER INFORMATION: synthetic

<400> SEQUENCE: 6
aaaaagactt agaaaaannt tt                                          22

<210> SEQ ID NO 7
<211> LENGTH: 22
<212> TYPE: DNA
<213> ORGANISM: Artificial Sequence
<220> FEATURE:
<221> NAME/KEY: modified_base
<222> LOCATION: (1)...(22)
<223> OTHER INFORMATION: n=5-iodo-deoxyurindine
<223> OTHER INFORMATION: synthetic

<400> SEQUENCE: 7
aaaaagacnn tgaaaaannn nt                                          22

<210> SEQ ID NO 8
<211> LENGTH: 27
<212> TYPE: DNA
<213> ORGANISM: Artificial Sequence
<220> FEATURE:
<223> OTHER INFORMATION: synthetic

<400> SEQUENCE: 8
aattcgcggc cgcaaaaaga cttgatc                                     27

<210> SEQ ID NO 9
<211> LENGTH: 23
<212> TYPE: DNA
<213> ORGANISM: Artificial Sequence
<220> FEATURE:
<223> OTHER INFORMATION: synthetic

<400> SEQUENCE: 9
gatcaagtct ttttgcggcc gcg                                         23

<210> SEQ ID NO 10
<211> LENGTH: 25
<212> TYPE: DNA
<213> ORGANISM: Artificial Sequence
<220> FEATURE:
<223> OTHER INFORMATION: synthetic

<400> SEQUENCE: 10
aattcgcggc cgcaaaaaga cttcg                                       25

<210> SEQ ID NO 11
<211> LENGTH: 21
<212> TYPE: DNA
<213> ORGANISM: Artificial Sequence
<220> FEATURE:
<223> OTHER INFORMATION: synthetic

<400> SEQUENCE: 11
cgaagtcttt ttgcggccgc g                                           21

<210> SEQ ID NO 12
<211> LENGTH: 22
<212> TYPE: DNA
```

```
<213> ORGANISM: Artificial Sequence
<220> FEATURE:
<223> OTHER INFORMATION: synthetic
<221> NAME/KEY: modified_base
<222> LOCATION: (0)...(0)
<223> OTHER INFORMATION: n=5-bromo-deoxyuridine

<400> SEQUENCE: 12
aaaaatnnnn cnaagtcttt nt                                    22

<210> SEQ ID NO 13
<211> LENGTH: 22
<212> TYPE: DNA
<213> ORGANISM: Artificial Sequence
<220> FEATURE:
<223> OTHER INFORMATION: synthetic
<221> NAME/KEY: modified_base
<222> LOCATION: (0)...(0)
<223> OTHER INFORMATION: n=5-iodo-deozyuridine

<400> SEQUENCE: 13
aaaaatnnnn caaagtcttt tt                                    22

<210> SEQ ID NO 14
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 14
aattcgcggc cgcaaaaaga cttgatc                               27

<210> SEQ ID NO 15
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 15
gatcaagtct ttttgcggcc gcg                                   23

<210> SEQ ID NO 16
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 16
aattcgcggc cgcaaaaaga cttgatcaag tcttttttgcg gccgcg         46

<210> SEQ ID NO 17
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 17
aattcgcggc cgcaaaaaga cttgatcaag tcttttttgcg gccgcg         46

<210> SEQ ID NO 18
<211> LENGTH: 22
<212> TYPE: DNA
<213> ORGANISM: Artificial Sequence
```

```
<220> FEATURE:
<223> OTHER INFORMATION: synthetic oligonucleotide

<400> SEQUENCE: 18
aaaaagactt agaaaaattt tt                                              22

<210> SEQ ID NO 19
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 19
aaaaattttt ctaagtcttt tt                                              22
```